United States Patent [19]

Giroir et al.

[11] Patent Number: 5,990,086
[45] Date of Patent: *Nov. 23, 1999

[54] THERAPEUTIC USES OF BPI PROTEIN PRODUCTS FOR HUMAN MENINGOCOCCEMIA

[75] Inventors: Brett P. Giroir, Dallas, Tex.; Patrick J. Scannon, San Francisco, Calif.

[73] Assignee: Xoma Corporation, Berkeley, Calif.

[*] Notice: This patent is subject to a terminal disclaimer.

[21] Appl. No.: 09/203,159

[22] Filed: Dec. 1, 1998

Related U.S. Application Data

[63] Continuation of application No. 08/927,437, Sep. 10, 1997, Pat. No. 5,888,977, which is a continuation of application No. 08/644,287, May 10, 1996, abandoned, which is a continuation-in-part of application No. 08/378,228, Jan. 24, 1995, Pat. No. 5,753,620, which is a continuation-in-part of application No. 08/291,112, Aug. 16, 1994, Pat. No. 5,643,875, which is a continuation-in-part of application No. 08/188,221, Jan. 24, 1994, abandoned.

[51] Int. Cl.$^6$ .......................... A61K 38/00; A61K 35/14
[52] U.S. Cl. .............................. 514/12; 514/21; 514/898; 530/324; 530/350; 530/829; 530/830; 424/529; 424/534
[58] Field of Search ................................ 514/12, 21, 898; 530/324, 350, 829, 830; 424/529, 534

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott et al. | 514/12 |
| 5,198,541 | 3/1993 | Elsbach | 435/69.1 |
| 5,234,912 | 8/1993 | Marra et al. | 514/21 |
| 5,245,013 | 9/1993 | Ulevitch et al. | 530/380 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,420,019 | 5/1995 | Theofan et al. | 435/69.1 |
| 5,439,807 | 8/1995 | Grinna | 435/69.1 |
| 5,447,913 | 9/1995 | Ammons et al. | 514/12 |
| 5,466,580 | 11/1995 | White et al. | 435/7.1 |
| 5,466,581 | 11/1995 | White et al. | 435/7.32 |
| 5,484,705 | 1/1996 | White et al. | 435/7.32 |
| 5,488,034 | 1/1996 | McGregor et al. | 514/12 |
| 5,494,896 | 2/1996 | Hansbrough | 514/12 |
| 5,523,288 | 6/1996 | Cohen et al. | 514/12 |
| 5,532,216 | 7/1996 | Espevik et al. | 514/21 |
| 5,576,292 | 11/1996 | Elsbach et al. | 514/12 |
| 5,578,568 | 11/1996 | Ammons et al. | 514/12 |
| 5,578,572 | 11/1996 | Horwitz et al. | 514/12 |

FOREIGN PATENT DOCUMENTS

| | | |
|---|---|---|
| WO 90/09183 | 8/1990 | WIPO . |
| WO 91/01639 | 2/1991 | WIPO . |
| WO 92/03535 | 3/1992 | WIPO . |
| WO 92/09621 | 6/1992 | WIPO . |
| WO 93/05797 | 4/1993 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |
| WO 94/20532 | 9/1994 | WIPO . |
| WO 94/21280 | 9/1994 | WIPO . |
| WO 94/25476 | 11/1994 | WIPO . |
| WO 95/00641 | 1/1995 | WIPO . |
| WO 95/01428 | 1/1995 | WIPO . |
| WO 95/02414 | 1/1995 | WIPO . |
| WO 95/08344 | 3/1995 | WIPO . |
| WO 95/08773 | 3/1995 | WIPO . |
| WO 95/10297 | 4/1995 | WIPO . |
| WO 95/19179 | 7/1995 | WIPO . |
| WO 95/19180 | 7/1995 | WIPO . |
| WO 95/19372 | 7/1995 | WIPO . |
| WO 95/19784 | 7/1995 | WIPO . |
| WO 95/20163 | 7/1995 | WIPO . |
| WO 95/24209 | 9/1995 | WIPO . |
| WO 96/01647 | 1/1996 | WIPO . |
| WO 96/08509 | 3/1996 | WIPO . |
| WO 96/21436 | 7/1996 | WIPO . |

OTHER PUBLICATIONS

Ammons et al., "Recombinant Amino Terminal Fragment of Bactericidal/ Permeability Increasing Protein Prevents Hemodynamic Responses to Endotoxin", *Circulatory Shock*, 41(3):176–184 (Nov., 1993).

Ammons et al., "Protective Effects of an N–Terminal Fragment of Bactericidal/Permeability–Increasing Protein in Rodent Models of Gram–Negative Sepsis: Role of Bactericidal Properties," *J. Infect. Dis.*, 170(6):1473–82 (Dec., 1994).

Ammons et al., "An N–Terminal Fragment of Bactericidal/ Permeability–Increasing Protein Protects against Hemodynamic and Metabolic Derangements in Rat Gram–Negative Sepsis," *J. Endotoxin Res.*, 3(1):57–66 (1996).

Ammons et al., "Protective Effects of an N–Terminal Fragment of Bactericidal/Permeability–Increasing Protein in Endotoxemia and Gram–Negative Sepsis," *Novel Therapeutics Strategies in the Treatment of Sepsis*, pp. 55–70 (1996).

Baggiolini et al., "Neutrophil–activating Peptide–1/Interleukin 8, a Novel Cytokine That Activates Neutrophils," *J. Clin. Invest.*, 84:1045–1049 (Oct., 1989).

Barron, "Pathophysiology of Septic Shock and Implications for Therapy," *Clinical Pharmacy*, 12(11):829–845 (Nov., 1993).

Berry, L.N., "Introduction" in *Handbook of Endotoxin, vol. 3, Cellular Biology of Endotoxin*, Berry, L.N., (Ed.), Elsevier, Amsterdam, New York, Oxford, pp. xvii–xxi, (1985).

(List continued on next page.)

*Primary Examiner*—Cecilia J. Tsang
*Assistant Examiner*—Abdel A. Mohamed
*Attorney, Agent, or Firm*—Marshall, O'Toole, Gerstein, Murray & Borun

[57] ABSTRACT

Methods and materials for the treatment of human meningococcemia are provided in which therapeutically effective amounts of BPI protein products are administered.

9 Claims, 6 Drawing Sheets

OTHER PUBLICATIONS

Binnema et al., "Quantitation of Urokinase Antigen in Plasma and Culture Media by Use of an Elisa," *Thromb. Res,* 43:569–577 (1986).

Bloom et al., "Serum Neopterin Levels Following Intravenous Endotoxin Administration to Normal Humans", *Immunobiol.,* 18:317–323 (1990).

Boermeester et al., "Bactericidal/Permeability–Increasing Protein (BPI) Prevents Hemodynamic and Metabolic Derangements Following Partial Hepatectomy," Dutch Society of Gastroenterology Meeting, p. 84 (Oct. 7, 1993) (Abstract).

Boermeester et al., "A Prophylactic Approach towards Postoperative Endotoxemia," in *Yearbook of Intensive Care and Emergency Medicine 1994,* Vincent, J.L., (Ed.), Springer–Verlag, pp. 35–41 (1994).

Boermeester et al., "Endotoxin and Interleukin–1 Related Hepatic Inflammatory Response Promotes Liver Failure After Partial Hepatectomy," *Hepatology,* 22(5):1499–15006 (Nov., 1995).

Boermeester et al., "Liver Failure Induces a Systemic Inflammatory Response," *Amer. J. Pathology,* 147(5):1428–1440 (Nov., 1995).

Bone, R.C., "The Pathogenesis of Sepsis," *Ann. Inter. Med.,* 115:457–469 (1991).

Bone et al., "Definitions for sepsis and organ failure", *Critical Care Medicine,* 20(6):724–726 (1992).

Boujoukos et al., "Detection of Interleukin–8 in Bronchoalveolar Lavage Without Alveolar Neutrophil Influx, Before and After Intravenous Endotoxin in Normal Humans", *Am. Rev. Resp. Dis.,* 145(4):A441 (Apr., 1992) (Abstract).

Boujoukos et al., "Compartmentalization of the acute cytokine response in humans after intravenous endotoxin administration", *J. Appl. Physiol.,* 74:3027–3033.

Bradley et al., "Hemodynamic Alterations in Normotensive and Hypertensive Subjects During the Pyrogenic Reaction", *J. Clin. Invest.,* 24:749–758 (1945).

Brandtzaeg et al., "Plasma Endotoxin as a Predictor of Multiple Organ Failure and Death in Systemic Meningococcal Disease," *J. Infect. Dis.,* 159(2):195–204 (Feb., 1989).

Brandtzaeg et al., "Plasminogen Activator Inhibitor 1 and 2, Alpha–2–Antiplasmin, Plasminogen, and Endotaxin Levels in Systemic Meningococcal Disease," *Thrombosis Research,* 57:271–278 (1990).

Brandtzaeg et al., "Meningococcal Endotoxin in Lethal Septic Shock Plasma Studied by Gas Chromatography, Mass–Spectrometry, Ultracentrifugation, and Electron Microscopy," *J. Clin. Invest.,* 89:816–823 (Mar., 1992).

Brandtzaeg et al., "Pathogenesis of Meningococcal Infections," in *Meningococcal Disease,* K. Cartwright, Ed., John Wiley & Sons, Ltd. pp. 72–114 (1995).

Brigham et al., "Endotoxin and Lung Injury", *Rev. Respir. Dis.,* 133:913–927 (1986).

Calandra et al., "Prognostic Values of Tumor Necrosis Factor/Cachectin, Interleukin–1, Interferon–α, and Interferon–γ in the Serum of Patients with Septic Shock", *J. Infect. Diseases,* 161:982–987 (May, 1990).

Calandra et al., "High Circulating Levels of Interleukin–6 in Patients with Septic Shock: Evolution During Sepsis, Prognostic Value, and Interplay with Other Cytokines", *Am. J. Medicine,* 91:23–29 (Jul., 1991).

Cannon et al., "Circulating Interleukin 1 and Tumor Necrosis Factor in Septic Shock and Experimental Endotoxin Fever", *J. Infect. Diseases,* 161:79–84 (Jan., 1990).

Cavaillon, J.M., "Controversies Surrounding Current Therapies for Sepsis Syndrome," *Bull. Inst. Pasteur.,* 93:21–41 (1995).

Chmielewska et al., "Evidence For a Rapid Inhibitor To Tissue Plasminogen Activation in plasma," *Thromb. Res.,* 31:427–436 (1983).

Cochrane, "The Enhancement of Inflammatory Injury", *Am. Rev. Respir. Dis.,* 136:1–2 (1980).

Colman, "Surface–mediated Defense Reactions, The Plasma Contact Activation System", *J. Clin. Invest.,* 73:1249–1253 (May, 1984).

Cross et al., "Choice of Bacteria in Animal Models of Sepsis," *Infect. Immun.,* 6(7):2741–2747 (Jul., 1993).

Cross, A.S., "Antiendotoxin Antibodies: A Dead End?" *Ann. Intern. Med.,* 121(1):58–60 (Jul. 1, 1994).

Danner et al., "Endotoxemia in Human Septic Shock", *Chest,* 99:169–175 (Jan. 1991).

de Winter et al., "Recombinant Endotoxin–Binding Protein (rBPI$_{23}$) Attenuates Endotoxin–Induced Circulatory Changes in Humans," *J. Inflamm.,* 45:193–206 (1995).

De La Cadena et al., "Activation of the Kallikrein–Kinin System After Endotoxin Administration to Normal Human Volunteers", *Blood,* 81(12):3313–3317 (Jun. 15, 1993).

Dinarello, C.A., "The Proinflammatory Cytokines Interleukin–12 and Tumor Necrosis Factor and Treatment of the Septic Shock Syndrome", *J. Infection Diseases,* 163:1177–1184 (Jun., 1991).

Edwards et al., "Complications and Sequelae of Meningococcal Infections in Children," *J. of Pediatrics,* 99(4):540–545 (Oct., 1981).

Elin et al., "Effect of Induced Fever on Serum Iron and Ferritin Concentrations in Man", *Blood,* 49(1):147–153 (Jan., 1977).

Elms et al., "Measurement of Crosslinked Fibrin Degardation Products–An Immunoassay Using Monoclonal Antibodies," *Thromb. Haemostas,* 50(2):591–594 (1983).

Elsbach et al. "Separation and Purification of a Potent Bactericidal/Permeability Increasing Protein and a Closely Associated Phopholipase A$_2$ from Rabbit Polymorphonuclear Leukocytes," *J. Biol. Chem.,* 254(21):11000–11009 (Nov., 1979).

Elsbach and Weiss, "Oxygen–Independent Antimicrobial Systems of Phagocytes," In *Inflammation: Basic Principles and Clinical Correlates,* Chapter 30, Second Edition, Gallin et al., (Eds.), Raven Press, Ltd., pp. 603–636, (1992).

Elsbach et al., "Prospects for Use of Recombinant BPI in the Treatment of Gram–Negative Bacterial Infections," *Infect. Agents Dis.,* 4:102–109 (1995).

Evans et al., "Protective Effects of a Recombinant Amino–Terminal Fragment of Human Bactericidal/Permeability–Increasing Protein in an Animal Model of Gram–Negative Sepsis," *J. Infect. Dis.,* 171:153–60 (Jan., 1995).

Fijnvandraat et al., "Endotoxin Induced Coagulation Activation and Protein C Reduction in Meningococcal Septic Shock," in *Bacterial Endotoxins: Basic Science to Anti–Sepsis Strategies,* Wiley–Liss, Inc., pp. 247–254 (1994).

Fink, M.P., "Adoptive Immunotherapy of Gram–Negative Sepsis: Use of Monoclonal Antibodies to Lipopolysaccharide," *Crit. Car.Med. (Supplement),* 21(2):S32–S39 (Feb., 1993).

Fiser, "Assessing the Outcome of Pediatric Intensive Care," *J. Pediatrics,* 121:168–174 (1992).

Fisher et al., "Human neutrophil bactericidal/permeability-increasing protein reduces mortality rate from endotoxin challenge: A placebo–controlled study," *Crit. Care Med.,* 2294):553–558 (Apr., 1994).

Fisher et al., "Recombinant Human Interleukin 1 Receptor Antagonist in the Treatment of Patients With Sepsis Syndrome: Results form a Randomized, Double–blind, Placebo–Controlled Trial," *JAMA,* 271(23):1836–1878 (Jun. 15, 1994).

Flaegstad et al., "Factors associated with fatal outcomes in childhood meningococcal disease," *Acta Paediatr.,* 84:1137–1142 (1995).

Fong et al., "Endotoxemia Elicits Increased Circulating β2–IFN/Il–6 in Man", *J. Immunology,* 142(7):2321–2324 (Apr. 1, 1989).

Fong et al., "Total Parental Nutrition and Bowel Rest Modify the Metabolic Response to Endotoxin in Humans", *Ann. Surg.,* 210(4):449–457 (Oct., 1989).

Fong et al., "The Acute Aplanchnic and Peripheral Tissue Metabolic Response to Endotoxin in Humans", *J. Clin. Invest.,* 85:1896–1904 (Jun. 1990).

Gazzano–Santoro et al., "High–Affinity Binding of the Bactericidal/Permeability–Increasing Protein and a Recombinant Amino–Terminal Fragment to the Lipid A Region of Lipopolysaccharide," *Infect. Immun.,* 60(11):4754–4761 (Nov., 1992).

Genoff et al., "Extremely Amputations in Meningococcal––Induced Purpura Fulminans," *Plastic Reconstructive Surg.,* 89(5):878–881 (May, 1992).

Giroir et al., "Meningococcal," in *Essentials of Pediatric Intensive Care,* Second Edition, vol. One, Levin, D.L. and Morris, F.C., Eds., Quality Medical Publishing, Inc., pp. 421–427 (1997).

Giroir et al., "Shock," in *Essentials of Pediatric Intensive Care,* Second Edition, vol. One, Levin D.L. and Morriss, F.C., Eds., Quality Medical Publishing, Inc., pp. 280–301 (1997).

Granowitz et al., "Production of interleukin–1–receptor antagonist during experimental endotoxaemia", *Lancet,* 338:1423–24 (Dec., 7, 1991).

Granowitz et al., "Hematologic and Immunomodulatory Effects of an Interleukin–1 Receptor Antagonist Coinfusion During Low–Dose Endotoxemia in Healthy Humans", *Blood,* 82(10):2985–2990 (Nov., 15, 1993).

Gray et al., "Cloning of the cDNA of a Human Neutrophil Bactericidal Protein," *J. Biol. Chem.,* 264(16):9505–9509 (Jun. 5, 1989).

Hack et al., "A Modified Competitive Inhibition Radioimmunoassay for the Detection of C3a Use of $^{125}$I–C3 Instead of $^{125}$I–C3A", *J. Immunol. Meth.,* 108:77–84 (1988).

Halstensen et al., "Sequelae One Year After Meningococcal Disease," *Acta. Neurol. Scand.,* 89:139–142 (1994).

Havens et al., "Trends in Mortality in Children Hospitalized With Meningococcal Infections,1957–1987," *Pediatr. Infect. Dis. J.,* 8(1):8–11 (1988).

Hesse et al., "Cytokine Appearance in Human Endotoxemia and Primate Bacteremia", *Srug., Gyn. & Obstet.,* 166:147–153 (Feb., 1988).

Hochberg, Y., "A sharper Bonferroni procedure for multiple tests of significance," *Biomtrika,* 75(4):800–802 (1988).

Hoffman et al., "Endotoxin in Septic Shock," *Anesth. Analg.,* 77:613–624 (1993).

Holvoet, P. et al., "Assay of Human Tissue–Type Plasminogen Activator (t–PA) with an Enzyme–Linked Immunosorbent Assay (ELISA) Based on Three Murine Monoclonal Antibodies to t–PA," *Thromb. Haemastasis.,* 54(3):684–687 (1985).

In't Veld., "Effects of the Bactericidal/Permeability–Increasing Protein of Polymorphonuclear Leukocytes on Isolated Bacterial Cytoplasmic Membrane Vesicles", *Infect. Immun.,* 56(5):1203–1208 (May, 1988).

Kelly et al., "Role of the bactericidal permeability–increasing protein in the treatment if gram–negative pneumonia", *Surgery,* 114(2):140–146 (Aug., 1993).

Kindt et al., "Initial recruitment of neutrophils to alveolar structures in acute lung injury", *J. Appl. Physiol.,* 70:1575–1585 (1991).

Kirsch, E. et al., "Pathophysiology, treatment and outcome of meningcoccemia: a review and recent experience," *Pediatr. Infect Dis J.,* 15(11):967–979 (1996).

Koch, G.G., "The Use of Non–Parametric Methods in the Statistical Analysis of the Two–Period Change–Over Design," *Biometric,* 28:577–584 (1972).

Kohn et al., "Protective Effect of a Recombinant Amino–Terminal Fragment of Bactericidal/Permeability–Increasing Protein in Experimental Endotoxemia", *J. Infect. Disease,* 168:1307–1310 (Nov., 1993).

Kohn et al., "Role of Endotoxin in Acute Inflammation Induced by Gram–Negative Bacteria:Specific Inhibition of Lipopolysaccharide–Mediated Responses with an Amino–Teminal Fragment of Bactericidal/Permeability–Increasing Protein," *Infect. Immun.,* 63(1):33–339 (Jan., 1995).

Koyama et al., "rBPI$_{23}$ Attenuates Endotoxin–Induced Cardiovascular Depression in Awake Rabbits," *Shock,* 4(1):74–78 (Jul., 1995).

Kung et al., "Efficacy of a recombinant terminal amino fragment of bactericidal/permeability increasing protein in rodents challenged with LPS or *E. coli* bacteria," in *Bacterial Endotoxins: Basic Science to Anti–Sepsis Strategies,* Wiley–Liss, Inc., New York, pp. 255–263 (1994).

Kung et al., "Pharmacokinetic Evaluations of rBPI$_{23}$ in Mice, Rats, and Humans," International Conference on Endotoxemia IV, Amsterdam, The Netherlands, p. 23, (Aug. 17–29, 1993) (Abstract P3).

Leach et al., "Prevention of Lethal Endotoxemia by BP$_{23}$ ", *J. Cell. Chem,* (Keystone Symposia, Suppl.) 16(C):172 (Feb. 21 –Mar. 7, 1992) (Abstract CB 412).

Lechner et al., "The Recombinant 23–kDa N–Terminal Fragment of Bactericidal/Permeability–Increasing Protein (rBPI$_{23}$) Decreases *Escherchia coli*–Induced Mortality and Organ Injury During Immunosuppression–Related Neutropenia," *Shock,* 4(4):298–306 (Oct., 1995).

Levi et al., "Reduction of Contact Activation Related Fibrinolytic Activity in Factor XII Deficient Patients," *J. Clin. Invest.,* 88:1155–1160 (Oct., 1991).

Levy et al., "Antibacterial 15–kDa Protein Isoforms (p15s) Are Members of a Novel Family of Leukocyte Proteins",*J. Biol. Chem.,* 268(8):6058–6063 (Mar., 1993).

Lichtman et al., "Reactivation of Arthritis Induced by Small Bowel Bacterial Overgrowth in Rats: Role of Cytokines, Bacteria, and Bacterial Polymers," *Infect. Immun.,* 63(6):2295–2301 (Jun., 1995).

Lin et al., "Protective Effect Of A Recombinant Fragment Of Bactericidal/Permeability–Increasing Protein Against Carbohydrate Dyshomeostasis And Tumor Necrosis Factor–α Elevation In Rate Endotoxemia," *Biochem. Pharmacol.* 47(9):1553–1559 (1994).

Lin et al., "Protective Effects of a Recombinant N–Terminal Fragment of Bactericidal/Permeability–Increasing Protein on Endotoxic Shokc in Conscious Rabbits," *Shock*, 2(5):324–3311 (Nov., 1994).

Lin et al., "Synergistic Effect of a Recombinant N–Terminal Fragment of Bactericidal/Permeability–Increasing Protein and Cefamandole in Treatment of Rabbit Gram–Negative Sepsis," *Antimicrobial Agents and Chemotherapy*, 40(1):65–69 (Jan., 1996).

MacIntyre et al., "E5 Antibody Improves Outcome from Multi–Organ Failure in Survivors of Gram–Negative Sepsis", *Critical Care Medicine*, S14 (Apr., 1991).

Mannion et al., "Separation of Sublethal and Lethal Effects of Polymorphonuclear Leukocytes on *Escherichia coli*", *J. Clin. Invest.*, 86:631–641 (Aug., 1990).

Marra et al., "Bactericidal/Permeability–Increasing Protein Has Endotoxin–Neutralizing Activity", *J. Immunol.*, 144(2):662–666 (Jan. 15, 1990).

Marra et al., "The Role of Bactericidal/Permeability–Increasing Protein as a Natural Inhibitor of Bacterial Endotoxin", *J. Immunol.*, 148(2):532–537 (Jan. 15, 1992).

Marra et al., "Endotoxin–binding and –neutralizing properties of recombinant bactericidal/permeability–increasing protein and monoclonal antibodies HA–1A and E4," *Crit. Care. Med.*, 22(4):559–565 (1994).

Martich et al., "Detection of Interleukin 8 and Tumor Necrosis Factor in Normal Humans after Intravenous Endotoxin: The Effect of Antiinflammatory Agents", *J. Exp. Medicine*, 173:1021–1024 (Apr., 1991).

Martich et al., "Effects of ibuprofen and pentoxifylline on the cardiovascular response of normal humans to endotoxin", *J. Appl. Physiol.*, 73(3):925–931 (1992).

Martich et al., "Intravenous Endotoxin Administration to Normal Humans Primes Neutrophils for an Enhanced Respiratory Burst", *Critical Care Medicine*, S100 (Apr., 1992).

Martich et al., "Response of Man to Endotoxin", *Immunobiol.*, 187(3):403–416 m (Apr., 1993).

McManus et al., "Coagulopathy as a Predictor of Outcome in Meningococcal Sepsis and the Systemic Inflammatory Response Syndrome With Purpura," *Critical Care Medicine*, 21(5):706–711 (1993).

Meszaros et al., "A Recombinant Amino Terminal Fragment of Bactericidal/Permeability–Increasing Protein Inhibits the Induction of Leukocyte Responses by LPS," *J. Leukocyte Biol.*, 54(6):558–563 (Dec., 1993).

Meszaros et al., "Monocyte Tissue Factor Induction by Lipopolysaccharide (LPS): Dependence on LPS–Binding Protein and CD14, and Inhibition by a Recombinant Fragment of Bactericidal/Permeability–Increasing Protein," *Blood*, 83(9):2516–2525 (May 1, 1994).

Michie et al., "Detection of Circulating Tumor Necrosis Factor After Endotoxin Administration", *N. Eng. J. Medicine*, 318(23):1481–1486 (Jun. 9, 1988).

Moore et al., "A Single Dose of Endotoxin Activates Neutrophils without Activating Complement", *Surgery*, 102(2):200–205 (Aug., 1987).

Moser et al., "Cardiopulmonary Consequencs of Pyrogen–Induced Hyperpyrexia in Man", *J. Clin. Invest.*, 42(5):626–634 (1963).

Nadel et al., "Treatment of Meningococcal Disease in Childhood," in *Meningococcal Disease*, Cartwright, ed., J. Wiley & Sons, New York, pp. 207–243 (1995).

Natanson et al., "Role of Endotoxemia in Cardiovascular Dysfunction and Mechanisms of Pathogenesis," *Ann. Inter. Med.*, 120(9):771–783 (May 1, 1994).

Niklasson et al., "Prognostic Factors in Meningococcal Diseasem" *Scand. J. Infect. Dis.*, 3:17–25 (1971).

Nuijens et al., "Plasma Elastase $\alpha_1$–antitrypsin and lactoferrin in sepsis: Evidence for neutrophils as mediators in fatal Sepsis", *J. Lab. Clin. Med.*, 119:159–168 (1992).

Ooi et al., "A 25–kDa $NH_2$–termianl Fragment Carries All the Antibacterial Activities of the Human Neutrophil 60–kDa Bactericidal/Permeability–increasing Protein," *J. Biol. Chem.*, 262(3):14891–14894 (1987).

Ooi et al., "Isolation of Two Isoforms of a Novel 15–kDa Protein from Rabbit Polymorphonuclear Leukocytes That Modulate the Antibacterial Actions of Other Leukocyte Proteins," *J. Biol. Chem.*, 265:15956–15962 (Sep. 15, 1990).

Ooi et al., "Endotoxin–neutralizing Properties of the 25 kDa N–Terminal Fragment and a Newly Isolated 30 KDC–Terminal Fragment of the 55–60 kD Bactericidal/Permeability–increasing Protein of Human Neutrophils," *J. Exp. Med.*, 174:649–655 (Sep., 1991).

Parker et al., "Profound but Reversible Myocardial Depression in Patients with Septic Shock," *Ann. Intern. Med.*, 100:483–490 (1984).

Parker et al., "Serial cardiovascular variables in surviors and nonsurviors of human septic shock: Heart rate as an early predictor of prognosis," *J. Crit. Care.*, 15(10):923–929 (1987).

Parrillo et al., "Septic Shock in Humans", *Annals of Int. Med.* 113(3):227–242 (Aug., 1990).

Peters et al., "Rapid Microanalysis of Coagulation Parameters by Automated Chromogenic Substrated Methods–Application in Neonatal Patients," *Thromb. Res.*, 28:773–781 (1982).

Petros et al., "Effects of a Nitric Oxide Synthase Inhibitor in Humans With Septic Shock," *Cardiovascular Research*, 28:34–39 (1994).

Pollack et al., "Pediatric Risk of Mortality (PRISM) Score," *Critical Care Medicine*, 16(11):1110–1116 (Nov. 1988).

Powars et al., "Epidemic Meningococcemia and Purpura Fulminans with Induced Protein C Deficiency," *Clinical Infectious Diseases*, 17:254–261 (1993).

Pruzanski et al., "Hyperphospholipasemia $A_2$ in Human Volunteers Challenged with Intravenous Endotoxin", *Inflammation* 16(5):561–570 (1992).

Quezado et al., "A Controlled Trial of HA–1A in a Canine Model of Gram–negative Septic Shock," *JAMA*, 269(17):2221–2227 (May 5, 1993).

Quezado et al., "New Strategies for Combating Sepsis: The Magic Bullets Missed the Mark . . . But the Search Continues," *TibTech*, 13:56–63 (Feb., 1995).

Rackow et al., "Hemodynamic Response to Fluid Repletion in Patients With Septic Shock: Evidence for Early Depression of Cardiac Performance," *Circ. Shock*, 22:11–22 (1987).

Revhaug et al., "Inhibition of Cyclo–oxygenase Attenuates the Metabolic Response to Endotoxin in Humans", *Arch. Surg.* 123:162–170 (Feb., 1988).

Scannon, P.J., "Applying Lessons Learned from Anti–Endotoxin Therapy," *J. Endo. Res.*, 2:217–220 (1995).

Schlag et al., "Protective Effect of Bactericidal/Permeability Increasing Protein ($rBPI_{21}$) on Sepsis Induced Organ Failure in Nonhuman Primates," *Shock Conference*, Ashville, N.C. Jun. 11–14, (1995) (Abstract).

Sheridan et al., "Management Strategy in Purpura Fulminans with Multiple Organ Failure in Children," *Burns*, 22(1):53–56 (1996).

Sinclair et al., "Prognosis of Meningococcal Septicaemia," *Lancet,* 2:38 (Jul. 4, 1987).

Smith et al., "Endotoxin Administration to Normal Huamns Causes Increased Alveolar Permeability and Priming of Alveolar Macrophages to Produce Enahanced Superoxide and IL–1 Production", *Clin. Res.* 36:374A (Apr., 1988) (Abstract).

Spinas et al., "Induction of plasma inhibitors of interleukin 1 and TNF–α activity by endotoxin administration to normal humans", *Am. J. Physiol.,* 259:R933–R997 (1990).

Spinas et al., "Pretreatment with Ibuprofen Augments Circulating Tumor Necrosis Factor–α , Interleukin–6, and Elastase during Acture Endotoxinemia", *J. Infectious Dis.,* 163:89–85 (1991).

Steven et al., "The Clinical Spectrum of Meningococcal Disease," in *Meningococcal Disease,* Cartwright, ed., J. Wiley & Sons, New York, pp. 178–205 (1995).

Stiehm & Damrosch, "Factors in the prognosis of meningococcla infection," *J. Pediatrics,* 68:457–467 (1966).

Sturk et al., "Optimalization of a Chromogenic Assay for Endotoxin in Blood," in *Bacterial Endotoxins: Structure, Biomedical Significance, and Detection with the Limulus Amebocyte Lysate Test,* pp. 117–136 (1985).

Suffredini et al., "Promotion and Subsequent Inhibition of Plasminogen Activation after Administration of Intravenous Endotoxin to Normal Subjects", *N. Eng. J. Medicine,* 320(18):1165–1172 (May 4, 1989).

Suffredini et al., "The Cardiovascular Response of Normal Humans to the Administration of Endotoxin", *N. Eng. J. Medicine,* 321:280–287 (Aug. 3, 1989).

Suffredini et al., "Pulmonary and Oxygen Transport Effects of Intravenously Administered Endotoxin in Normal Humans", *Am. Rev. Respir. Dis.,* 145:1398–1403 (1992).

Suffredini et al., "Current Prospects for the Treatment of Clinical Sepsis," *Crit. Care Med.,* 22(7):S12–S18 (Jul., 1994).

Teitel et al., "Studies of the Prothrombin Activation Pathway Utilizing Radioimmunoassays for the $F_2/F_{1+2}$ Fragment and Thrombin–Antithrombin Complex," *Blood,* 59(5):1086–1096 (May, 1982).

Tesoro et al., "Factors Affecting Outcome in Meningococcal Infections," *AJDC,* 145:218–220 (Feb., 1991).

Thornton et al., "Bactericidal/Permeability–Increasing Protein Inhibits Tumor Necrosis Factor Release in Whole Blood in Response to *Neisseria Meningitidis* and *N. Gonorrhoeae,*" *FASEB J.,* 8(4):A137 (1994) (Abstract 794).

van Deventer et al., "Experimental Endotoxemia in Humans: Analysis of Cytokine Release and Coagulation, Fibrinolytic, and Complement Pathways", *Blood,* 76(12):2520–2526 (Dec. 15, 1990).

Van Dueren et al., "Correlation between Proinflammatory Cytokines and Antiinflammatory Mediators and the Severtiy of Disease in Meningococcal Infections," *J. Infect. Dis.,* 172:433–439 (1995).

van Leeuwan et al., "Hepatic Failure and Coma After Liver Resection is Reversed by Manipulation of Gut Contents: The Role of Endotoxin," *Surgery,* 110(2):169–175 (Aug., 1991).

Van Zee et al., "Tumor necrosis factor soluble receptors circulate during experimental and clinical inflammation and can protect against excessive tumor necrosis factor, α in vitro and in vivo", *Proc. Natl. Acad. Sci. USA.,* 89:4845–4849 (Jun., 1992).

Van Zee et al., "Tumor Necrosis Factor (TNF) Soluble Receptors Protect Against Excessive TNFα During Infection and Injury", *Fed. Amer. Soc. Exp. Biol.,* 6:A1715 (1992) (Abstract 4512).

VanderMeer et al., "Bactericidal/Permeability–Increasing Protein Ameliorates Acute Lung Injury in Porcine Endotoxemia," *J. Infect. Dis.,* 172(1):2006–14 (May 1994).

Verheijen et al., "A Simple, Sensitive Spectrophotometric Assay for Extrinsic (Tissue–Type) Plasminogen Activator Applicable to Measurements in Plasma," *Thromb. Haemostas,* 48(3):266–269 (1982).

von der Möhlen et al., "Effect of $rBPI_{23}$ on Endotoxin–induced Cytokine Release and Leukocyte Changes in Human Volunteers" *Clinical Research,* 42(2):152A (Apr., 1994) (Abstract).

Waage et al., "The Complex Pattern of Cytokines in Serum from Patients with Meningococcal Septic Shock", *J. Exp. Med.* 169:33–338 (Jan., 1989).

Weiss et al., "Resistance of Gram–negative Bacteria to Purified Leukocyte Proteins", *J. Clin. Invest.,* 65:619–628 (Mar., 1980).

Weiss et al., "The Role of Lipopolysaccharide in the Action of the Bactericidal/Permeability Neutrophil Protein on the Bacterial Envelope", *J. Immunol.,* 132:3109–3115 (Jun., 1984).

Weiss et al., "Cellular and Subcellular Localization of the Bactericidal/Permeability–Increasing Protein of Neutrophils," *Blood,* 69(2):652–659 (Feb., 1987).

Weiss et al., "Tissue Destruction by Neutrophils", *N. Eng. J. Medicine,* 320(6):365–376 (Feb. 9, 1989).

Weiss et al., "Human Bacterial/Permeability–increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria," *J. Clin. Invest.,* 90:1122–1130 (Sep., 1992).

Wolff, "Biological Effects of Bacterial Endotoxins in Man", *J. Infectious Diseases* 128(Supplement):S259–S264 (Jul., 1973).

Wong et al., "Meningococcal Infections in Children: As Review of 100 Cases," *Pediatr. Infect. Dis. J.,* 8(4):224–227 (1989).

Yao et al., "Pathogenesis of Hemorrhage–Induced Bacteria/Endotoxin Translocation in Rats," *Annals Surg.,* 221(4):398–405 (Apr., 1995).

Yong et al., "An Experiment Mouse Model of Yersinia–induced Reactive Arthritis," *Microbiol Path.,* 4:304–310 (1988).

Yong et al., "Protective Effect of Re–LPS Antiserum on Experimental Multiple System Organ Failure," *Chinese Medical Journal,* 105(10):833–838 (Oct. 1992).

Zabel et al., "Oxpentifylline in Endotoxaemia", *Lancet,* 2:1474–1477 (Dec. 23/30, 1989).

Kartalija et al., "Effect of Recombinant N–Terminal Fragment of Bactericidal/Permeability–Increasing Protein (rBPI–23) on Cerespinal Fluid Inflammation Induced by Endotoxin," *J. Infectious Diseases,* 171(4):948–953 (Apr. 1995).

Kirch et al., "Phase I/II Trial of rBPI–21 (A Recombinant 21kDa Fragment of Bactericidal/Permeability–Increasing Protein) in Children With Severe Meningococcemia," *Pediatric Research,* 41(4):35A (Apr., 1997).

Thornton et al., The FASEB Journal, vol. 8, No. 4, Mar. 15, 1994, Abstract No. 794, p. A137.

Marijke et al., Blood, vol. 85, No. 2 pp. 3437–3443, Jun. 15, 1995.

Marijke et al., The Journal of Infectious Diseases, vol. 172, pp. 144–151, Jul. 1995.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1813 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 31..1491

(ix) FEATURE:
      (A) NAME/KEY: mat_peptide
      (B) LOCATION: 124..1491

(ix) FEATURE:
      (A) NAME/KEY: misc_feature
      (D) OTHER INFORMATION: "rBPI"

(xi) SEQUENCE DESCRIPTION: SEQ ID NO:1:

```
CAGGCCTTGA GGTTTTGGCA GCTCTGGAGG ATG AGA GAG AAC ATG GCC AGG GGC        54
                                 Met Arg Glu Asn Met Ala Arg Gly
                                 -31 -30                     -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
            -20                 -15                 -10

GGC ACC GCC GTG ACA GCG GCC GTC AAC CCT GGC GTC GTG GTC AGG ATC        150
Gly Thr Ala Val Thr Ala Ala Val Asn Pro Gly Val Val Val Arg Ile
        -5                   1               5

TCC CAG AAG GGC CTG GAC TAC GCC AGC CAG CAG GGG ACG GCC GCT CTG        198
Ser Gln Lys Gly Leu Asp Tyr Ala Ser Gln Gln Gly Thr Ala Ala Leu
10              15                  20                  25

CAG AAG GAG CTG AAG AGG ATC AAG ATT CCT GAC TAC TCA GAC AGC TTT        246
Gln Lys Glu Leu Lys Arg Ile Lys Ile Pro Asp Tyr Ser Asp Ser Phe
                30                  35                  40

AAG ATC AAG CAT CTT GGG AAG GGG CAT TAT AGC TTC TAC AGC ATG GAC        294
Lys Ile Lys His Leu Gly Lys Gly His Tyr Ser Phe Tyr Ser Met Asp
                45                  50                  55

ATC CGT GAA TTC CAG CTT CCC AGT TCC CAG ATA AGC ATG GTG CCC AAT        342
Ile Arg Glu Phe Gln Leu Pro Ser Ser Gln Ile Ser Met Val Pro Asn
            60                  65                  70

GTG GGC CTT AAG TTC TCC ATC AGC AAC GCC AAT ATC AAG ATC AGC GGG        390
Val Gly Leu Lys Phe Ser Ile Ser Asn Ala Asn Ile Lys Ile Ser Gly
    75                  80                  85

AAA TGG AAG GCA CAA AAG AGA TTC TTA AAA ATG AGC GGC AAT TTT GAC        438
Lys Trp Lys Ala Gln Lys Arg Phe Leu Lys Met Ser Gly Asn Phe Asp
90                  95                  100                 105

CTG AGC ATA GAA GGC ATG TCC ATT TCG GCT GAT CTG AAG CTG GGC AGT        486
Leu Ser Ile Glu Gly Met Ser Ile Ser Ala Asp Leu Lys Leu Gly Ser
                110                 115                 120

AAC CCC ACG TCA GGC AAG CCC ACC ATC ACC TGC TCC AGC TGC AGC AGC        534
Asn Pro Thr Ser Gly Lys Pro Thr Ile Thr Cys Ser Ser Cys Ser Ser
                125                 130                 135

CAC ATC AAC AGT GTC CAC GTG CAC ATC TCA AAG AGC AAA GTC GGG TGG        582
His Ile Asn Ser Val His Val His Ile Ser Lys Ser Lys Val Gly Trp
                140                 145                 150
```

-continued

| | | |
|---|---|---|
| CTG ATC CAA CTC TTC CAC AAA AAA ATT GAG TCT GCG CTT CGA AAC AAG<br>Leu Ile Gln Leu Phe His Lys Lys Ile Glu Ser Ala Leu Arg Asn Lys<br>155                      160                      165 | 630 |
| ATG AAC AGC CAG GTC TGC GAG AAA GTG ACC AAT TCT GTA TCC TCC AAG<br>Met Asn Ser Gln Val Cys Glu Lys Val Thr Asn Ser Val Ser Ser Lys<br>170                      175                      180                      185 | 678 |
| CTG CAA CCT TAT TTC CAG ACT CTG CCA GTA ATG ACC AAA ATA GAT TCT<br>Leu Gln Pro Tyr Phe Gln Thr Leu Pro Val Met Thr Lys Ile Asp Ser<br>                      190                      195                      200 | 726 |
| GTG GCT GGA ATC AAC TAT GGT CTG GTG GCA CCT CCA GCA ACC ACG GCT<br>Val Ala Gly Ile Asn Tyr Gly Leu Val Ala Pro Pro Ala Thr Thr Ala<br>                  205                      210                      215 | 774 |
| GAG ACC CTG GAT GTA CAG ATG AAG GGG GAG TTT TAC AGT GAG AAC CAC<br>Glu Thr Leu Asp Val Gln Met Lys Gly Glu Phe Tyr Ser Glu Asn His<br>            220                      225                      230 | 822 |
| CAC AAT CCA CCT CCC TTT GCT CCA CCA GTG ATG GAG TTT CCC GCT GCC<br>His Asn Pro Pro Pro Phe Ala Pro Pro Val Met Glu Phe Pro Ala Ala<br>235                                    240                      245 | 870 |
| CAT GAC CGC ATG GTA TAC CTG GGC CTC TCA GAC TAC TTC TTC AAC ACA<br>His Asp Arg Met Val Tyr Leu Gly Leu Ser Asp Tyr Phe Phe Asn Thr<br>250                      255                      260                      265 | 918 |
| GCC GGG CTT GTA TAC CAA GAG GCT GGG GTC TTG AAG ATG ACC CTT AGA<br>Ala Gly Leu Val Tyr Gln Glu Ala Gly Val Leu Lys Met Thr Leu Arg<br>                      270                      275                      280 | 966 |
| GAT GAC ATG ATT CCA AAG GAG TCC AAA TTT CGA CTG ACA ACC AAG TTC<br>Asp Asp Met Ile Pro Lys Glu Ser Lys Phe Arg Leu Thr Thr Lys Phe<br>                          285                      290                      295 | 1014 |
| TTT GGA ACC TTC CTA CCT GAG GTG GCC AAG AAG TTT CCC AAC ATG AAG<br>Phe Gly Thr Phe Leu Pro Glu Val Ala Lys Lys Phe Pro Asn Met Lys<br>                  300                      305                      310 | 1062 |
| ATA CAG ATC CAT GTC TCA GCC TCC ACC CCG CCA CAC CTG TCT GTG CAG<br>Ile Gln Ile His Val Ser Ala Ser Thr Pro Pro His Leu Ser Val Gln<br>315                      320                      325 | 1110 |
| CCC ACC GGC CTT ACC TTC TAC CCT GCC GTG GAT GTC CAG GCC TTT GCC<br>Pro Thr Gly Leu Thr Phe Tyr Pro Ala Val Asp Val Gln Ala Phe Ala<br>330                      335                      340                      345 | 1158 |
| GTC CTC CCC AAC TCC TCC CTG GCT TCC CTC TTC CTG ATT GGC ATG CAC<br>Val Leu Pro Asn Ser Ser Leu Ala Ser Leu Phe Leu Ile Gly Met His<br>                  350                      355                      360 | 1206 |
| ACA ACT GGT TCC ATG GAG GTC AGC GCC GAG TCC AAC AGG CTT GTT GGA<br>Thr Thr Gly Ser Met Glu Val Ser Ala Glu Ser Asn Arg Leu Val Gly<br>                      365                      370                      375 | 1254 |
| GAG CTC AAG CTG GAT AGG CTG CTC CTG GAA CTG AAG CAC TCA AAT ATT<br>Glu Leu Lys Leu Asp Arg Leu Leu Leu Glu Leu Lys His Ser Asn Ile<br>            380                      385                      390 | 1302 |
| GGC CCC TTC CCG GTT GAA TTG CTG CAG GAT ATC ATG AAC TAC ATT GTA<br>Gly Pro Phe Pro Val Glu Leu Leu Gln Asp Ile Met Asn Tyr Ile Val<br>395                      400                      405 | 1350 |
| CCC ATT CTT GTG CTG CCC AGG GTT AAC GAG AAA CTA CAG AAA GGC TTC<br>Pro Ile Leu Val Leu Pro Arg Val Asn Glu Lys Leu Gln Lys Gly Phe<br>410                      415                      420                      425 | 1398 |
| CCT CTC CCG ACG CCG GCC AGA GTC CAG CTC TAC AAC GTA GTG CTT CAG<br>Pro Leu Pro Thr Pro Ala Arg Val Gln Leu Tyr Asn Val Val Leu Gln<br>                      430                      435                      440 | 1446 |
| CCT CAC CAG AAC TTC CTG CTG TTC GGT GCA GAC GTT GTC TAT AAA<br>Pro His Gln Asn Phe Leu Leu Phe Gly Ala Asp Val Val Tyr Lys<br>                  445                      450                      455 | 1491 |
| TGAAGGCACC AGGGGTGCCG GGGGCTGTCA GCCGCACCTG TTCCTGATGG GCTGTGGGGC | 1551 |
| ACCGGCTGCC TTTCCCCAGG GAATCCTCTC CAGATCTTAA CCAAGAGCCC CTTGCAAACT | 1611 |

```
TCTTCGACTC AGATTCAGAA ATGATCTAAA CACGAGGAAA CATTATTCAT TGGAAAAGTG      1671

CATGGTGTGT ATTTTAGGGA TTATGAGCTT CTTTCAAGGG CTAAGGCTGC AGAGATATTT      1731

CCTCCAGGAA TCGTGTTTCA ATTGTAACCA AGAAATTTCC ATTTGTGCTT CATGAAAAAA      1791

AACTTCTGGT TTTTTTCATG TG                                               1813
```

(2) INFORMATION FOR SEQ ID NO:2:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Glu Asn Met Ala Arg Gly Pro Cys Asn Ala Pro Arg Trp Val
-31 -30              -25                 -20

Ser Leu Met Val Leu Val Ala Ile Gly Thr Ala Val Thr Ala Ala Val
-15              -10                  -5                      1

Asn Pro Gly Val Val Arg Ile Ser Gln Lys Gly Leu Asp Tyr Ala
              5                  10                  15

Ser Gln Gln Gly Thr Ala Ala Leu Gln Lys Glu Leu Lys Arg Ile Lys
             20                  25                  30

Ile Pro Asp Tyr Ser Asp Ser Phe Lys Ile Lys His Leu Gly Lys Gly
             35                  40                  45

His Tyr Ser Phe Tyr Ser Met Asp Ile Arg Glu Phe Gln Leu Pro Ser
 50              55                  60                      65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
                 85                  90                  95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
            115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
            195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
            230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
            260                 265                 270

Gly Val Leu Lys Met Thr Leu Arg Asp Asp Met Ile Pro Lys Glu Ser
275                 280                 285
```

```
Lys Phe Arg Leu Thr Thr Lys Phe Phe Gly Thr Phe Leu Pro Glu Val
290                 295             300             305

Ala Lys Lys Phe Pro Asn Met Lys Ile Gln Ile His Val Ser Ala Ser
            310             315             320

Thr Pro Pro His Leu Ser Val Gln Pro Thr Gly Leu Thr Phe Tyr Pro
            325             330             335

Ala Val Asp Val Gln Ala Phe Ala Val Leu Pro Asn Ser Ser Leu Ala
        340             345             350

Ser Leu Phe Leu Ile Gly Met His Thr Thr Gly Ser Met Glu Val Ser
    355             360             365

Ala Glu Ser Asn Arg Leu Val Gly Glu Leu Lys Leu Asp Arg Leu Leu
370             375             380                     385

Leu Glu Leu Lys His Ser Asn Ile Gly Pro Phe Pro Val Glu Leu Leu
            390             395             400

Gln Asp Ile Met Asn Tyr Ile Val Pro Ile Leu Val Leu Pro Arg Val
            405             410             415

Asn Glu Lys Leu Gln Lys Gly Phe Pro Leu Pro Thr Pro Ala Arg Val
            420             425             430

Gln Leu Tyr Asn Val Val Leu Gln Pro His Gln Asn Phe Leu Leu Phe
    435             440             445

Gly Ala Asp Val Val Tyr Lys
450             455
```

THERAPEUTIC USES OF BPI PROTEIN PRODUCTS FOR HUMAN MENINGOCOCCEMIA

This is a Continuation of U.S. application Ser. No. 08/927,437, filed Sep. 10, 1997, now U.S. Pat. No. 5,888,977 which is a Continuation of U.S. application Ser. No. 08/644,287 filed May 10, 1996, now abandoned which is a continuation-in-part application of U.S. Ser. No. 08/378,228, filed Jan. 24, 1995, now U.S. Pat. No. 5,753,620, which in turn is a continuation-in-part application of U.S. Ser. No. 08/291,112, filed Aug. 16, 1994, which in turn is a continuation-in-part application of U.S. Ser. No. 08/188,221, filed Jan. 24, 1994, now abandoned all of which are incorporated herein by reference.

BACKGROUND OF THE INVENTION

The present invention relates generally to methods and materials for treating humans suffering from meningococcemia by administration of bactericidal/permeability-increasing (BPI) protein products.

Meningococcemia is an infectious disease caused by *Neisseria meningitidis* (also known as meningococcus) in which the bacteria and their products are found in the systemic circulation. Its clinical course varies from a relatively mild process to a severe, fulminant infection of sudden onset and extremely rapid progression, with the time from first fever until death spanning as little as 12 hours. The latter, dramatic form of the disease occurs in about 10% of patients infected with *N. meningitdis*. Patients may present with normal mental status and symptoms only of fever and petechiae, but may rapidly experience hemodynamic collapse, loss of the airway, and coma, along with severe coagulopathy, intravascular thrombosis, and organ failure. Alternatively, in late stages of the disease, patients may be unconscious and unresponsive at the time of presentation.

The mortality rate for acute meningococcal disease has not changed significantly over the last few decades despite technological advances in antibiotics and intensive care facilities. One retrospective study found that the mortality rate from meningococcal infection had not changed significantly over 30 years, even after adjusting for disease severity [Havens et al., *Pediatr. Infect. Dis. J.*, 8:8–11 (1989)]. Another prospective study of meningococcal infections [Powars et al., *Clin. Infect. Dis.*, 17:254–261 (1993)] in the years 1986 through 1991 reported that 113 patients with bacteriologically proven *N. meningitdis* infection were observed, of whom 15 (13%) died. This mortality rate of 13% had not changed appreciably from the mortality rate of 16% reported five decades earlier in a Chilean epidemic. An "epidemic" is defined as an increased frequency of disease due to a single bacterial clone spread through a population. Although epidemics of meningococcemia are widespread in the developing world, no national epidemic has occurred in the United States since the 1940's. However, a significant increase in the endemic occurrence of meningococcemia, along with localized epidemics has occurred in the mid-1990s. The disease continues to be seasonal, with peak incidence in the late winter and early spring. Between 60% and 90% of all cases occur in children, with the peak incidence in children under age 2.

*N. meningitidis* is an encapsulated gram-negative coccus, typically occurring in pairs (diplococci), which is responsible for a spectrum of severe diseases, including meningococcemia. Meningococci are divided into nine serogroups on the basis of their capsular polysaccharides, with serogroups A, B, C, Y, and W135 accounting for the majority of clinical disease. These serogroups are further subdivided into antigenically distinct serotypes on the basis of expression of outer membrane proteins. Specific clones within each serogroup can be further delineated by protein electrophoretic patterns. The outer membrane of meningococci also contains a form of lipopolyaccharide (LPS), i.e., "lipooligosaccharide" (LOS), which is a common component of the outer membrane of gram-negative bacteria.

The meningococcus is known to colonize the nasopharynx of 5–15% of individuals; however, only a small fraction of those colonized will experience invasive disease. The transition from colonization to invasive disease is multifactorial and incompletely understood. The presence of viral upper-respiratory infections, which also peak during the late winter and spring, may damage the nasopharyngeal epithelium and permit bacterial translocation across an altered barrier. In children under 2 years of age, inadequate development of antibodies directed against the meningococcal polysaccharide capsule is thought to account for the high attack rate in this population.

The spectrum of disease caused by the meningococcus includes meningitis, arthritis, pericarditis, endocarditis, conjunctivitis, endophthalmitis, respiratory tract infections, abdominal and pelvic infections, urethritis, and a chronic bacteremic syndrome. The predominant clinical syndromes requiring pediatric intensive care unit (PICU) admission are meningitis and meningococcemia (with or without meningitis). The clinical presentation depends on the compartment of the body in which the infection and its inflammatory sequelae are primarily localized.

In contrast to meningococcemia, meningitis is a disease in which the bacteria are localized to the meningeal compartment, with signs consistent with meningeal irritation. Clinically, meningococcal meningitis is dramatically different from meningococcemia, however, it may be indistinguishable from other forms of meningitis, and only differentiated by culture or immunologic assays. Systemic hemodynamic signs, severe coagulopathy and intravascular thrombosis are notably absent. If properly treated, mortality is rare and neurologic sequelae, including sensineural hearing loss, is uncommon. The approach to diagnosis and treatment of meningococcal meningitis is the same as with other forms of bacterial meningitis.

If patients are examined early in the course of their disease when only petechiae and mild constitutional symptoms are evident, the diagnosis of meningococcemia may be complicated by the number of diseases which present with fever and petechiae in children, including, for example, infections by enterovirus, rotavirus, respiratory syncytial virus, *Haemophilus influenzae*, or *Streptococcus pneumoniae*; streptococcal pharyngitis; Rocky Mountain spotted fever, Henoch-Schoenlein purpura; or malignancy. However, since the outcome of meningococcal disease is highly dependent on rapid diagnosis and institution of antibiotics, the suspicion of meningococcemia must be aggressively pursued and treatment instituted, particularly since *H. influenza* meningitis has markedly decreased in the United States due to use of the vaccine against the bacteria.

Like other gram negative infections, the pathogenesis of severe meningococcemia is initiated by the endotoxin on, associated with or released from the bacteria. This bacterial endotoxin activates the pro-inflammatory cytokine cascade. In severe meningococcemia, the levels of bacterial endotoxin detected in the circulation by the LAL assay have been documented to be as much as 50–100 fold greater than levels documented in other gram negative infections. The complement cascade is also activated by bacteria and their endotoxin in the systemic circulation, producing anaphylotoxins which may mediate early hypotension and capilary leak.

In studies thus far, plasma levels of endotoxin [Brandtzaeg et al., *J. Infec. Dis.*, 159:195–204 (1989)], TNF [Van Deuren et al., *J. Infect. Dis.*, 172:433–439 (1995)], IL-6 [Van Deuren et al., supra], and fibrinogen, as well as prothrombin time (PTT) [McManus et al., *Critical Care Med.*, 21:706–711 (1993)] in meningococcemia patients have been correlated with the severity and outcome of disease, although the correlation is imprecise. It has been suggested that combining ranked values for endotoxin, TNF, IL-1 and IL-6 can achieve a score that accurately reflects patient outcome [Bone, *Critical Care Med.*, 22:S8–S11 (1994)].

Severe coagulopathy and intravascular thrombosis may be rapidly progressive and lead to ischemic injury of extremities and vital organs in meningococcemia patients. Respiratory failure, renal failure, adrenal failure and coma may develop. Petechiae and purpura may be extensive and become confluent, in which case the term "purpura fulminans" has been applied. In meningococcemic patients with severe disease, significant reductions in the coagulation inhibitors antithrombin III, activated protein C, and protein S have also been documented. These reductions may reflect a relative imbalance of anti-coagulant factors compared to pro-coagulants, but may also reflect the general consumption of all classes of factors. Quantitative deficiencies may also reflect hemodilution and capillary leak of proteins.

Severe cardiac dysfunction is often present on admission, or may develop within the first 24 hours. Ejection fractions of 20% or less are freuent. Cardiac dysfunction may be secondary to a number of factors, including: 1) myocarditis, which is present to varying degrees in a majority of autopsy specimens; 2) myocardial depressant substances; 3) intravascular thrombosis and subsequent myocardial ischemia; 4) myocardial interstitial edema, resulting in a non-compliant ventricle; 5) hypoxic myocardial injury; and 6) metabolic abnormalities.

Hypotension and circulatory insufficiency are multifactorial, with significant contributions from intravascular volume depletion, capillary leak, profound vasodilation (secondary to anaphylotoxins, nitric oxide, histamine, and other mediators), and depressed myocardial performance. Organ damage secondary to hypotension, intravascular thrombosis, and direct inflammatory damage may be evident at presentation.

Fulminant disease may be associated with adrenal hemorrhage, adrenal cortical necrosis, and rapid demise (Waterhouse Friederickson Syndrome). Even extensive adrenal hemorrhages, however, do not necessarily denote adrenal insufficiency, since normal or even elevated systemic cortisol levels have been documented in such patients. In a minority of patients with rapidly progressive disease, adrenal hemorrhages are associated with serum cortisol levels which are normal or subnormal (in a setting where elevated levels are expected). Other metabolic derangements such as metabolic acidosis, hypoglycemia, hypocalcemia, and hypomagnesemia are also frequently present.

Patients with severe disease are at highest risk of mortality. If they survive, they often experience severe morbidities, including extensive tissue and bone destruction that requires debridement and/or amputation followed by skin grafting procedures. In one study [Powars et al., supra], among the 28 patients with purpura fulminans, the hallmark of severe meningococcemia, 14 patients (50%) died. Of the 14 surviving patients who had purpura fulminans, 10 suffered soft tissue gangrene with deforming autoamputation. In another report [Genoff et al., *Plastic Reconstructive Surg.*, 89:878–881 (1992)], six patients with meningococcemia and purpura fulminans were followed, of whom four patients required severe amputations (wrist or above for the upper limbs, or ankle or above for the lower limbs). Genoff et al. note that even after the life-threatening acute phase of the disease has passed, complications continue and require revisions to a higher level of amputation and multiple grafting procedures. Sheridan et al., *Burns*, 22:53–56 (1996), confirms that meningococcernia with purpura fulminans has a reported mortality rate of 50%, with high rates of major amputations in survivors. In their experience, surviving patients are often left with full thickness wounds involving the skin, subcutaneous tissue and often underlying muscle and bone; half of the surviving patients require major amputations.

Patients with meningococcal disease may also develop neurologic sequelae, including electroencephalogram (EEG) abnormalities, computerized tomography (CT) scan abnormalities, hearing impairment and neuropsychological testing deficits. In one study, 99 consecutive children and adult patients with acute, bacteriologically confirmed meningococcal disease were followed and tested for neurologic sequelae one year after their illness. [Naess et al., *Acta Neuron. Scand.*, 89:139–142 (1994).] In the category of patients suffering from meningococcemia with hypotension and/or ecchymoses, but without signs of meningitis, neurologic sequelae were observed in 5 of the 12 patients. In the category of patients suffering from meningococcemia with hypotension and/or ecchymoses, and with signs of meningitis, neurologic sequelae were observed in 7 of 13 patients.

Clinical outcome can be reasonably predicted by scoring of risk factors originally identified in large cohorts of meningococcemia patients. In 1966, Stiehm and Damrosh, *J. Pediatrics*, 68:457–467 (1966), reviewed 63 cases of meningococcal infection and identified clinical features associated with poor outcome. Poor prognostic factors included: onset of petechiae within 12 hours prior to admission, absence of meningitis (cerebrospinal fluid (CSF) WBC<20), shock (systolic blood pressure<70), normal or low white blood count (WBC <10,000), and normal or low erythrocyte sedimentation rate (<10 mm/hr). The presence of 3 or more of these criteria was associated with poor outcome. Niklasson et al., *Scand. J. Infect. Dis.*, 3:17–25 (1971), substantiated these risk factors in 1971, and added temperature>40° C. and thrombocytopenia to the list of poor prognostic signs. The specific predictive abilities of the Stiehm and Damrosh criteria and the Niklasson criteria have been challenged in a series from McManus [McManus et al., supra] in 1993.In this series, mortality was significantly less than predicted by earlier criteria and was more likely related to the presence or absence of coagulopathy.

The most widely used meningococcal sepsis scoring system was published in 1987 by Sinclair et al., *Lancet*, 2:38 (1987), and has become known as the Glasgow Meningococcal Septicemia Prognostic Score (Glasgow score). Its utility stems from its reliance on bedside clinical indicators, which facilitates triage in the field or during transport. Points are given on a rated scale for seven parameters as follows: (1) BP<75 mm Hg systolic, age<4 years or BP<85 mm Hg systolic, age>4 years (3 points); (2) skin/rectal temperature difference>3° C. (3 points); (3) modified coma scale<8, or deterioration of 3 or more points in 1 hour (3 points); (4)

deterioration in hour before scoring (2 points); (5) absence of meningism (2 points); (6) extending purpura or widespread ecchymoses (1 point); and (7) base deficit (capillary or arterial)>8 (1 point). The maximum Glasgow score is therefore 15 points.

Since meningococcemia is frequently characterized by rapid and fuliniant deterioration, vigilant monitoring is mandated. The great majority of patients should be admitted directly to the intensive care unit, where invasive monitoring can be instituted, and supportive therapy provided. Specific additions to monitoring and laboratory evaluation may include obtaining samples from CSF, blood cultures, skin lesions and throat swabs. However, CSF should be obtained only if the patient's clinical condition is stable enough to tolerate the procedure. Blood cultures should be obtained, but are positive in only 50% of untreated patients. Bacteria can also be detected in up to 70% of cases by Gram stain and culture of aspirated (or biopsied) hemorrhagic skin lesions. Examination of skin lesions is especially important for cases in which antibiotics have been administered prior to obtaining blood cultures. Throat swabs, if carefully obtained and rapidly plated, may also yield meningococci and support a presumptive diagnosis of meningococcemia. Alternatively, CSF may be obtained for detection of meningococcal antigens. If an organism is obtained, it should be serotyped and forwarded to a reference laboratory for additional subtyping. Epidemic control through immunization can only occur if the specific organisms responsible for disease are identified. In the unusual circumstance in which blood cultures cannot be obtained, antibiotics should still be administered without delay; microbiologic investigation can be accomplished at a later time by alternate methods.

Management of children with meningococcemia relies on intensive, aggressive monitoring and therapy. In particular, early protection of the airway, aggressive volume replacement, and appropriate institution of vasoactive agents, e.g., epinephrine, dopamine and dobutamine, are critical to restore tissue perfusion and oxygen delivery. A few specific issues in the treatment of meningococcemia, including treatment with antibiotics, steroids, fresh frozen plasma (FFP) replacement, heparin, and several new agents are briefly highlighted below.

An ongoing debate continues concerning whether antibiotics should be administered as soon as the diagnosis is suspected or after a period of stabilization. Although not resolved by randomized trials, the preponderance of evidence suggests that antibiotics should be administered immediately, while other supportive therapies are being instituted. Speculations regarding a post-antibiotic release of bacterial endotoxin in meningococcemia have not been substantiated by human data. Serial quantitation of bacterial endotoxin levels in plasma samples from humans with meningococcemia have failed to demonstrate a post-antibiotic surge in plasma endotoxin levels.

Initial therapy of suspected cases currently is typically recommended to be a third generation cephalosporin (e.g. Ceftriaxone) until other causes of severe infectious purpura with shock have been ruled out (*H. influenza, S. pneumoniae*, other gram negative bacteria). Therapy can then be switched to parenteral penicillin or ampicillin.

To date, there are currently no randomized, placebo controlled data to support the routine use of corticosteroids in patients with meningococcemia. However, data have demonstrated that a minority of patients with severe disease and adrenal hemorrhage exhibit normal or subnormal levels of plasma cortisol (in a situation during which elevated levels are expected). Although the lack of data precludes an affirmative or negative recommendation, the physician should consider administering adrenal replacement steroids (hydrocortisone 1-2 mg/kg i.v.) in a clinical situation of rapidly progressive shock that is unresponsive to fluids and inotropes.

There have also been to date no randomized, placebo controlled data to determine whether, or to what degree, biochemical coagulopathy should be treated with FFP. Although correction of biochemical abnormalities may appear logical, administration of FFP has been viewed by many as "fueling the fire" of coagulopathy. In a case-control trial of 336 patients in Norway, treatment with plasma or blood products (as opposed to albumin or plasma substitutes) was independently associated with poorer outcome. A surge in plasma endotoxin was also documented in a C6 deficient human following FFP administration during treatment for meningococcemia. These data suggest that administration of FFP may be harmful in some situations and therefore should be done carefully and only when there are compelling clinical indications.

Although small retrospective reports advocate the use of heparin as a treatment for purpura fulminans, the preponderance of data (small randomized trials and large case-control studies) do not indicate a beneficial effect of heparin therapy. There is currently no evidence to support the routine use of heparin in the treatment of meningococcemia. A large scale, double-blind, placebo-controlled Phase III trial of a monoclonal anti-lipid A antibody (HA-1A) in meningococcemia has been conducted in Europe. No results have been published to date.

In addition, a number of other biological agents are candidates for treatment of severe coagulopathy and intravascular thrombosis. These agents include: antithrombin III, protein C, and tissue factor pathway inhibitor. Anecdotal experiences with protein C and antithrombin m have already been published pending definitive trials. Other clinical interventions have been reported but have not been systematically tested, including: plasma and whole blood exchange, leukaplasmapheresis, continuous caudal blockade to relieve lower extremity ischemia, and topical application of nitroglycerin to vasodilate the peripheral vascular bed.

BPI is a protein isolated from the granules of mammalian polymorphonuclear leukocytes PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 1 hereto. U.S. Pat. No. 5,198,541 discloses recombinant genes encoding and methods for expression of BPI proteins, including BPI holoprotein and fragments of BPI.

BPI is a strongly cationic protein. The N-terminal half of BPI accounts for the high net positive charge; the C-terminal half of the molecule has a net charge of −3.[Elsbach and Weiss (1981), supra.] A proteolytic N-termninal fragment of BPI having a molecular weight of about 25 kD possesses essentially all the anti-bacterial efficacy of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et al., *Infect. Immun.* 60:4754–4761 (1992).

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Esbach and Weiss (1992), supra]. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

BPI has never been used previously for the treatment of subjects infected with *N. meningitidis*, including subjects suffering from meningococcemia. In co-owned, co-pending U.S. application Ser. Nos. 08/378,228, filed Jan. 24, 1995, 08/291,112, filed Aug. 16, 1994, and 08/188,221, filed Jan. 24, 1994, incorporated herein by reference, the administration of BPI protein product to humans with endotoxin in circulation was described. [See also, von der Möhlen et al., *J. Infect. Dis.* 172:144–151 (1995); von der Möhlen et al., *Blood* 85:3437–3443 (1995); de Winter et al., *J. Inflam.* 45:193–206 (1995)]. Thornton et al., *FASEB J.*, 8(4):A137, 1994, report that BPI inhibited the release of TNF in vitro by human inflammatory cells in response to LOS derived from two Neisseria species, *N. meningitidis* and *N. gonorrhea*; and the report in International Application Publication No. WO 94/25476 published Nov. 10, 1994, of methods of treating endotoxin-related disorders, including Gram-negative meningitis.

In spite of treatment with antibiotics and state-of-the-art medical intensive care therapy, the mortality and morbidities associated with human meningococcemia remain significant and unresolved by current therapies. New therapeutic methods are needed that could reduce or ameliorate the adverse events and improve the clinical outcome of human meningococcemia, including, for example, reducing mortality, amputations, grating procedures, permanent neurologic impairment and improving pediatric outcome scores.

SUMMARY OF THE INVENTION

The present invention provides novel methods for treatment of humans with meningococcemia involving the administration of BPI protein products to provide clinically verifiable alleviation of the adverse effects of, or complications associated with, this human disease, including mortality and morbidities.

According to the invention, BPI protein products such as rBPI$_{21}$ are administered to humans suffering from meningococcemia in amounts sufficient to prevent mortality and/or to reduce the number or severity of morbidities, including but not limited to amputations, grafting procedures and/or permanent neurologic impairment.

Numerous additional aspects and advantages of the invention will become apparent to those skilled in the art upon consideration of the following detailed description of the invention which describes presently preferred embodiments thereof.

DETAILED DESCRIPTION

Figure 1:
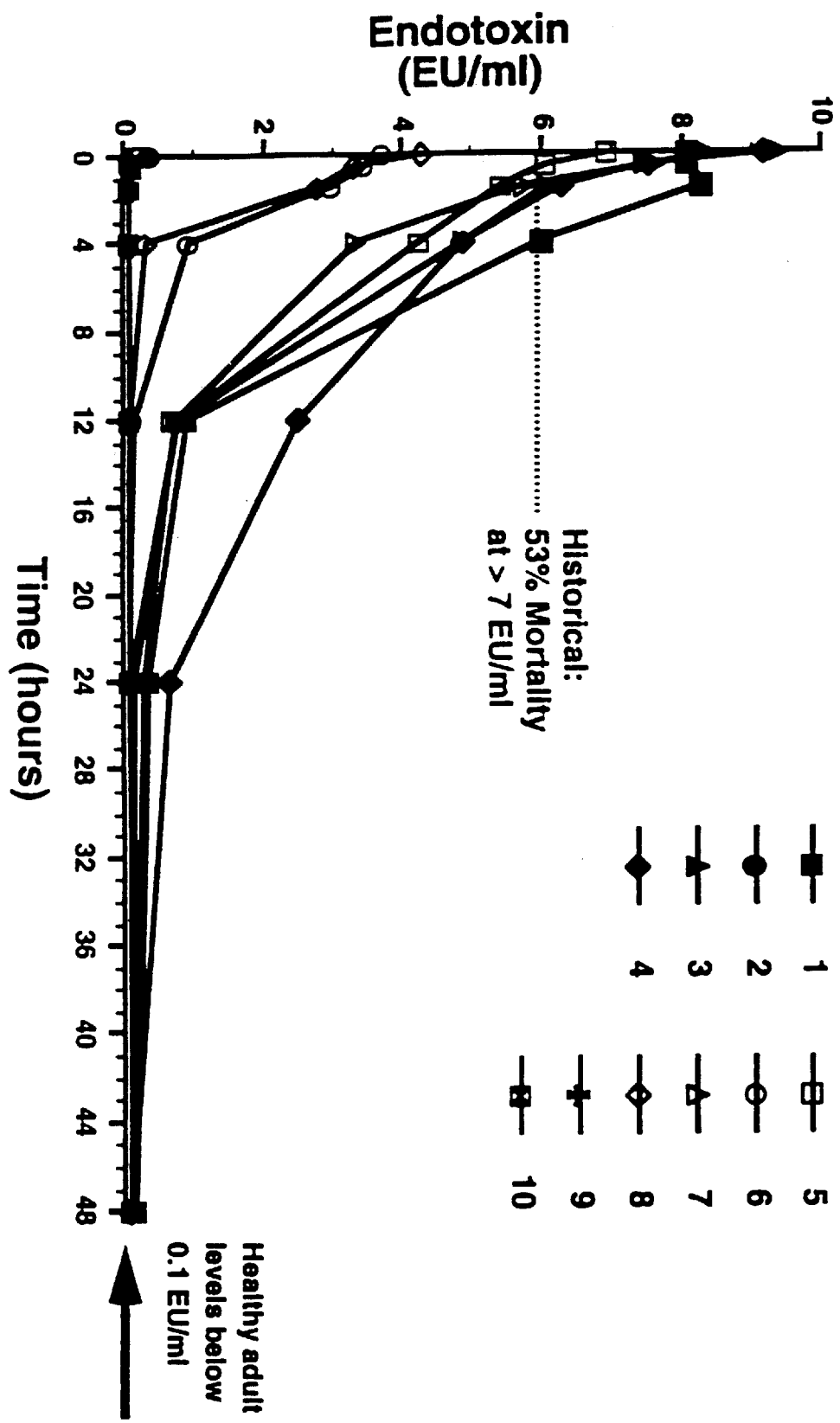
FIGS. 1, 3 and 5 depict plasma levels of endotoxin, TNF and IL-6, respectively, over time for the initial ten patients enrolled in the BPI study.
Figure 2:
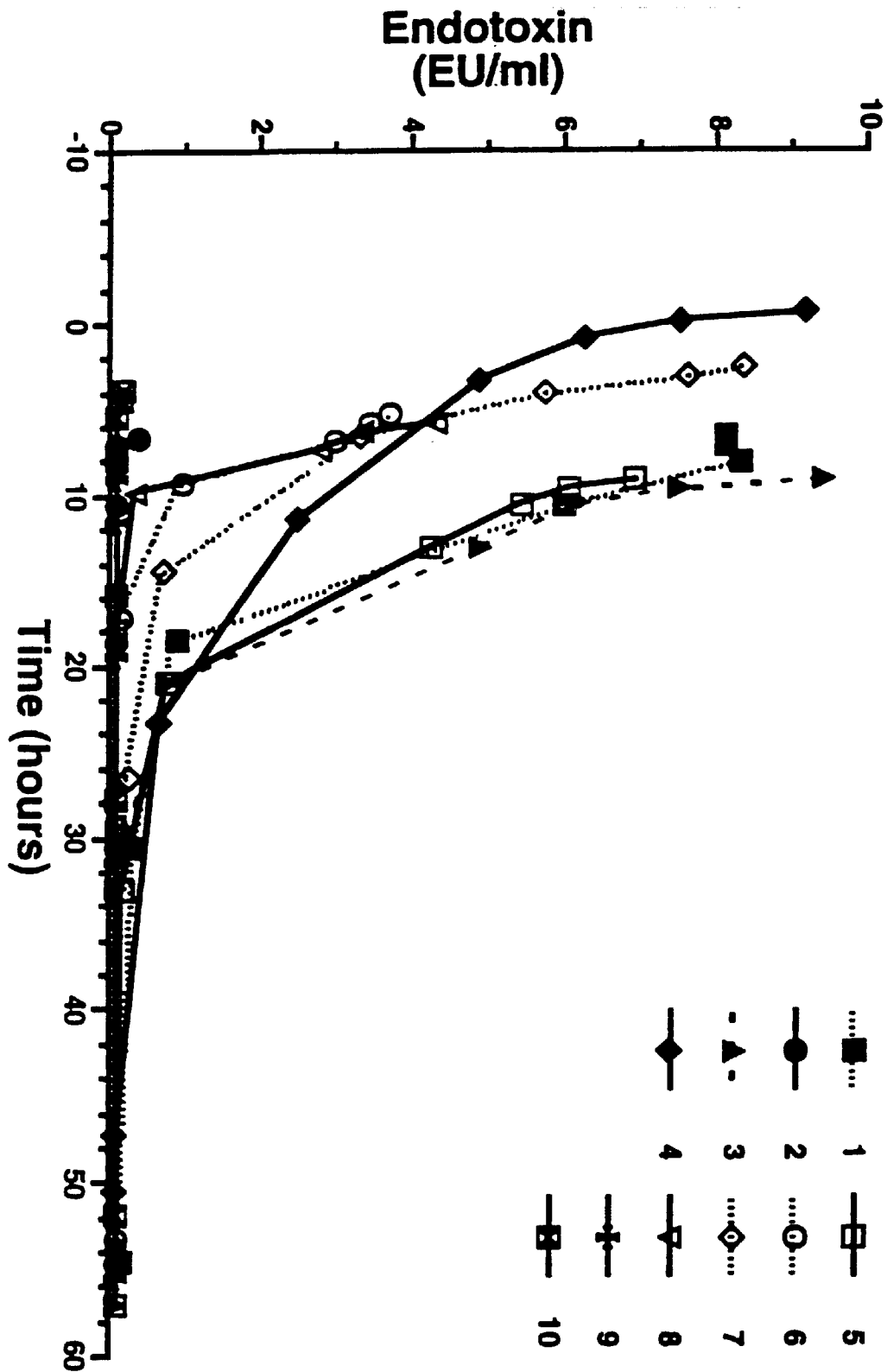
FIGS. 2, 4 and 6 depict the plasma endotoxin, TNF and IL-6 levels displayed in FIGS. 1, 3 and 5, respectively, offset for each patient by the time between initiation of antibiotic treatment and initiation of BPI protein roduct therapy.
Figure 3:
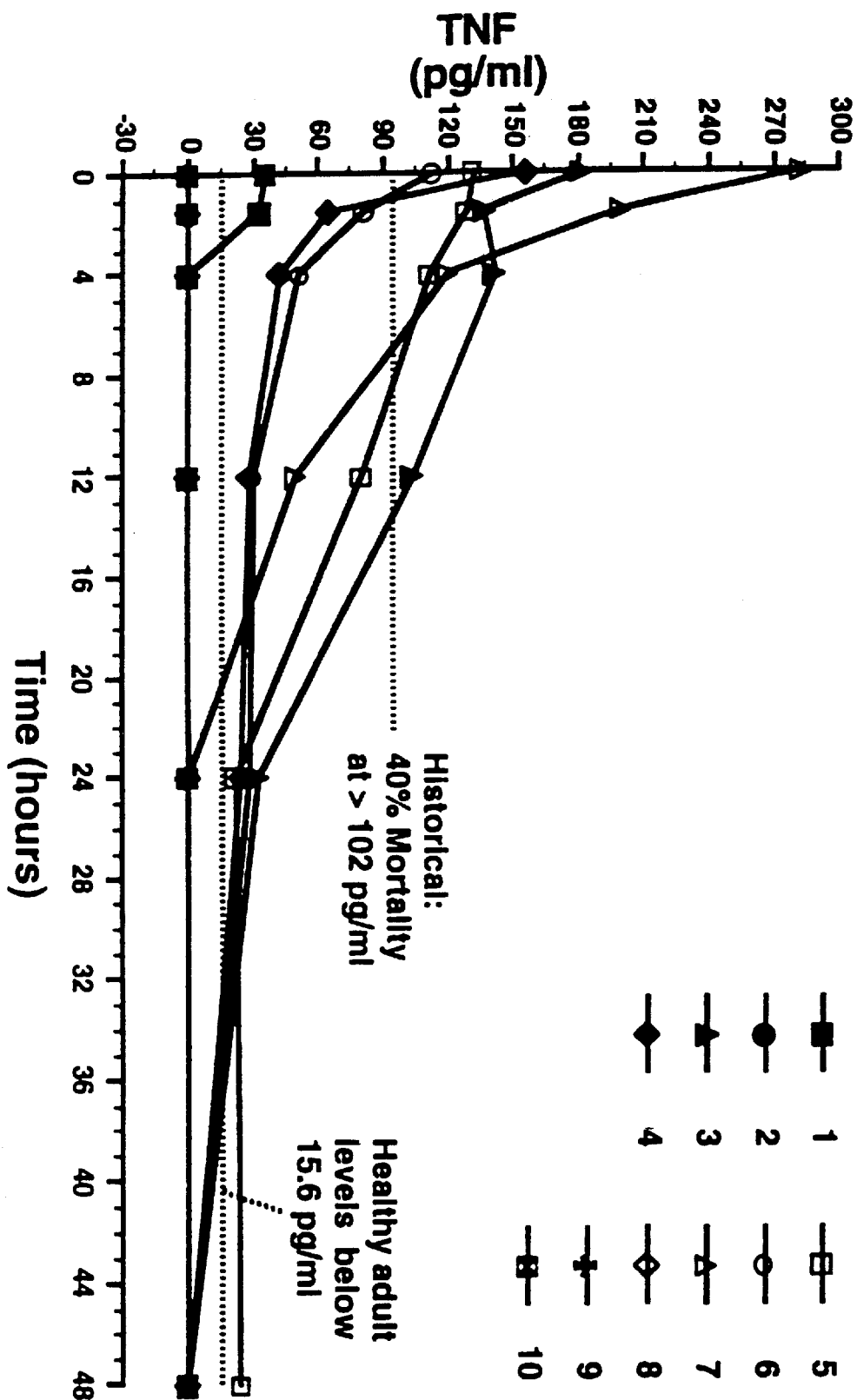
Figure 4:
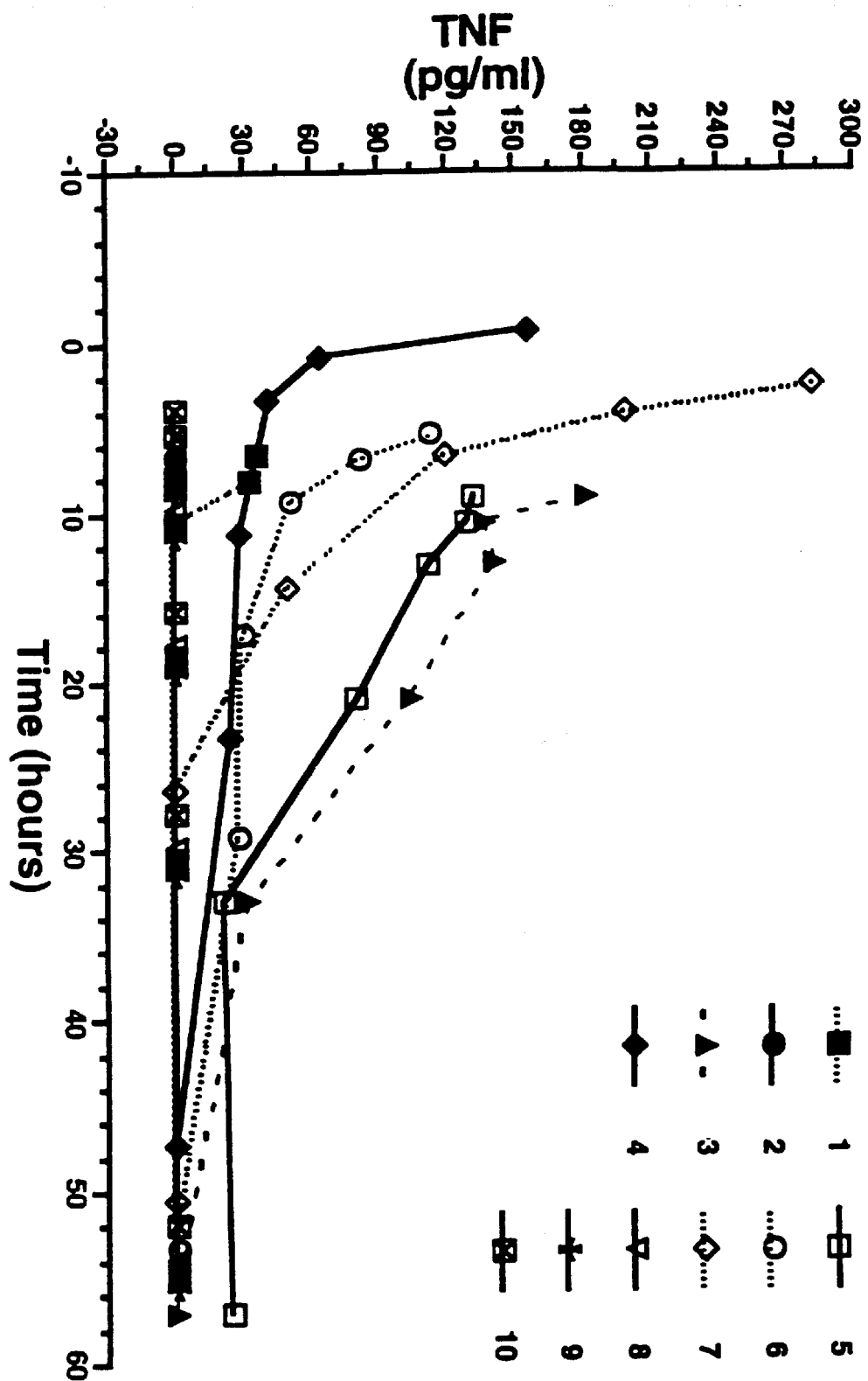
Figure 5:
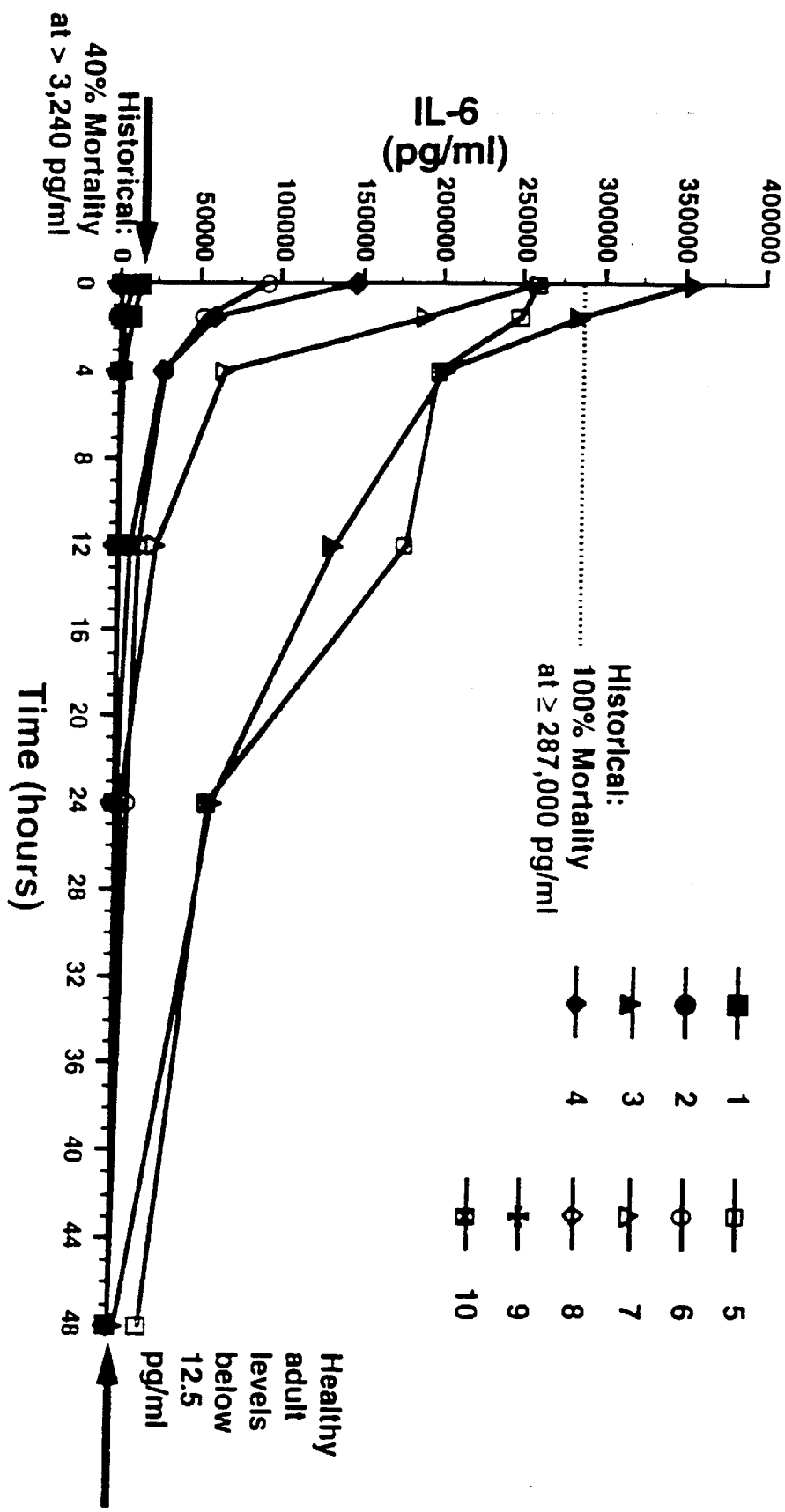
Figure 6:
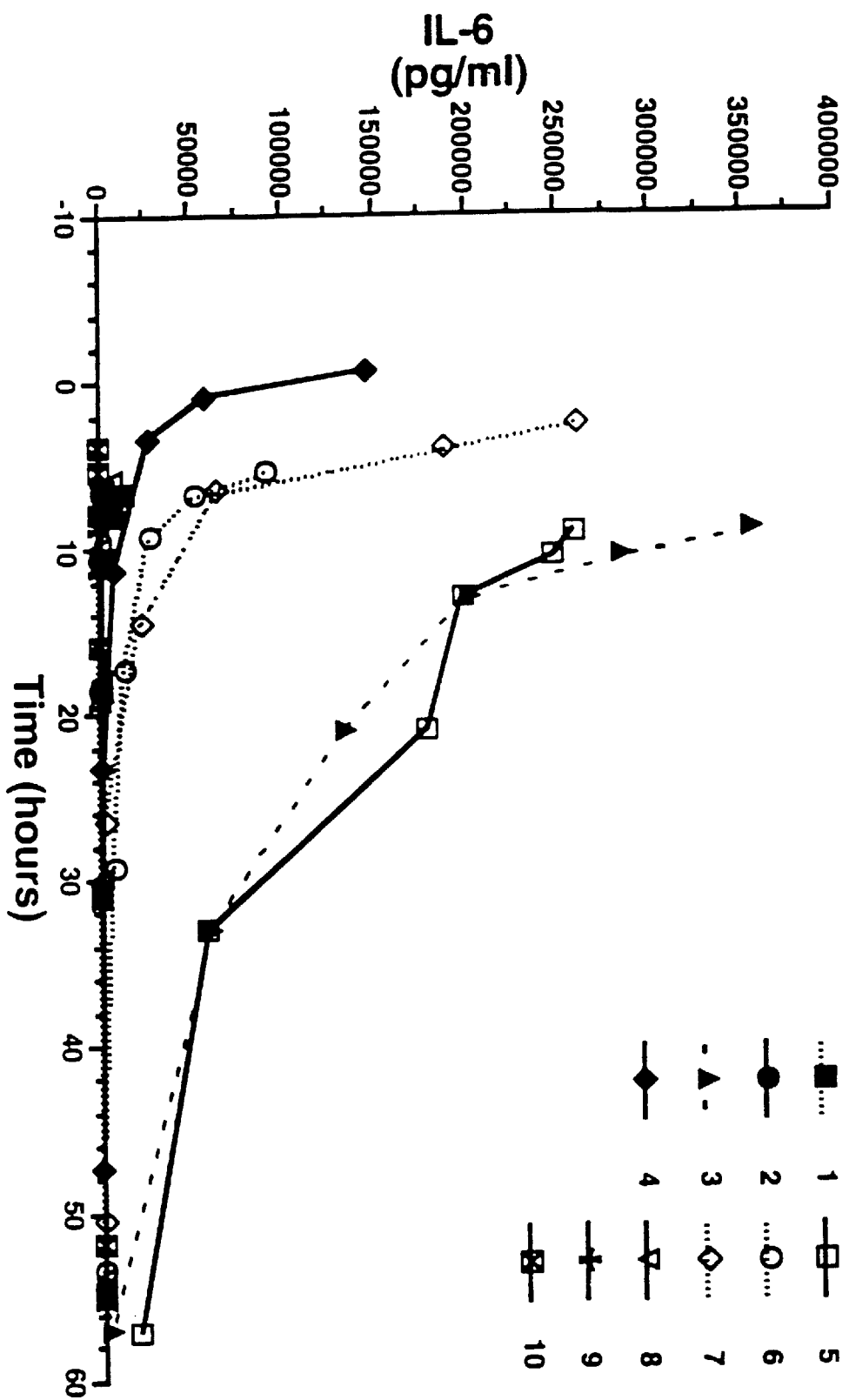

Human meningococcemia is an increasingly prevalent, life-threatening, debilitating disease for which conventional antibiotics and intensive care are inadequate. In particular, significant mortality and severe morbidities have remained in spite of state-of-the-art medical intensive care. It has now been unexpectedly found that the administration of BPI protein products to humans with meningococcemia has effectively decreased mortality and reduced the number and severity of morbidities, including amputations, debridement of dead tissue followed by extensive grafting procedures, and/or permanent neurologic impairment resulting in significant and long-term impairment of neurologic function (e.g., cerebrovascular accidents, cerebral atrophy, or seizures requiring medication). These unexpected effects on the mortality and morbidities associated with and resulting from meningococcemia demonstrate that BPI protein products have effectively interfered with or blocked a number of the multiple poorly-understood pathophysiologic processes that have led to poor outcomes in this human disease.

BPI protein products are expected to provide other beneficial effects for meningococcemia patients, such as reduced number of episodes of hypotension or cardiac arrhythmia or arrest, reduced length of time on ventilatory support and inotropic (vasoactive) therapy, reduced duration and severity of associated coagulopathy, reduced stay in the ICU, and reduced incidence of complications such as respiratory failure, renal failure, coma, adrenal cortical necrosis, pericarditis, endocarditis, cardiomyopathy, endophthalmitis, and arthritis.

BPI protein products have been demonstrated to have a bactericidal effect in vitro against serogroups A, B, C and W135 of the gram-negative bacteria, *Neisseria meningitidis*, that causes meningococcemia. BPI protein products may exert their effect in human meningococcemia through such direct bactericidal action, or through enhancing the effectiveness of antibiotic therapy as described in co-owned, co-pending U.S. application Ser. No. 08/311,611 filed Sep. 22, 1994, which issued U.S. Pat. No. 5,523,288 on Jun. 4, 1996, and which is incorporated herein by reference. BPI protein products may also exert their effect in human meningococcemia through neutralizing LOS endotoxin that has been released from or remains in association with the bacteria and bacterial fragments. The effects of BPI protein products in humans with endotoxin in circulation, including effects on TNF, IL-6 and endotoxin is described in co-owned, co-pending U.S. application Ser. No. 08/378,228, filed Jan. 24, 1995, which in turn is a continuation-in-part application of U.S. Ser. No. 08/291,112, filed Aug. 16, 1994, which in turn is a continuation-in-part application of U.S. Ser. No. 08/188,221, filed Jan. 24, 1994, all of which are incorporated herein by reference. BPI protein products exhibit both anticoagulant and fibrinolytic effects, as described in co-owned, co-pending U.S. application Ser. No. 08/644,290 filed concurrently herewith, which is incorporated herein by reference. BPI protein products may act on other pathologic processes that accompany meningococcemia including, for example, coagulopathies.

Therapeutic compositions comprising BPI protein product may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal lavage), intrapulmonary using aerosolized or nebulized drug, or transdermal. The preferred route is intravenous administration. When given parenterally, BPI protein product compositions are generally injected in doses ranging from 1 µg/kg to 100 mg/kg per day, preferably at doses ranging from 0.1 mg/kg to 20 mg/kg per day, more preferably at doses ranging from 1 to 20 mg/kg/day and most preferably at doses ranging from 2 to 10 mg/kg/day. The treatment may continue by continuous infusion or intermittent injection or infusion, at the same, reduced or increased dose per day for, e.g., 1 to 3 days, and additionally as determined by the treating physician. BPI protein products are preferably administered intravenously by an initial bolus followed by a continuous infusion. The preferred regimen is a 1 to 20 mg/kg intravenous bolus of BPI protein product followed by intravenous infusion at a dose of 1 to 20 mg/kg/day, continuing for up to one week. The most preferred dosing regimen is a 2 to 10 mg/kg initial bolus followed by intravenous infusion at a dose of 2 to 10 mg/kg/day, continuing for up to 72 hours. Topical routes include administration in the form of salves, ophthalmic drops, ear drops, irrigation fluids (for, e.g., irrigation of wounds) or medicated shampoos. For example, for topical administration in drop form, about 10 to 200 µL of a BPI protein product composition may be applied one or more times per day as determined by the treating physician. Those skilled in the art can readily optimize effective dosages and administration regimens for therapeutic compositions comprising BPI protein product, as determined by good medical practice and the clinical condition of the individual patient.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as rBPI$_{50}$ (or rBPI) and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT application Ser. No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI$_{50}$) has also been produced having the sequence (SEQ ID NOS: 1 and 2) set out in FIG. 1 of Gray et al., supra, with the exceptions noted for rBPI$_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, filed Mar. 11, 1994, and corresponding PCT application Ser. No. PCT/US95/03125, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated rBPI$_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064, 693 filed May 19, 1993 and corresponding PCT application Ser. No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof. Similarly configured hybrid fusion proteins involving part or all Lipopolysaccharide Binding Protein (LBP) are also contemplated for use in the present invention.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT application Ser. No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. co-owned and co-pending U.S. patent application Ser. No. 08/212,132 filed Mar. 11, 1994, and corresponding PCT application Ser. No. PCT/US95/03125, the disclosures of which are incorporated herein by reference.

Other BPI protein products useful according to the methods of the invention are peptides derived from or based on BPI produced by recombinant or synthetic means (BPI-derived peptides), such as those described in co-owned and co-pending U.S. patent application Ser. No. 08/504,841 filed Jul. 20, 1995 and in co-owned and copending PCT application Ser. No. PCT/US94/10427 filed Sep. 15, 1994, which corresponds to U.S. patent application Ser. No. 08/306,473 filed Sep. 15, 1994, and PCT application Ser. No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT application Ser. No. US94/02401 filed Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantly-produced N-terminal fragments of BPI, especially those having a molecular weight of approximately between 21 to 25 kD such as $rBPI_{23}$ or $rBPI_{21}$, or dimeric forms of these N-terminal fragments (e.g., $rBPI_{42}$ dimer). Additionally, preferred BPI protein products include $rBPI_{50}$ and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-microbial agents. One pharmaceutical composition containing BPI protein products (e.g., $rBPI_{50}$, $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another pharmaceutical composition containing BPI protein products (e.g., $rBPI_{21}$, ) comprises the BPI protein product at a concentration of 2 mg/mL in 5 mM citrate, 150 mM NaCl, 0.2% poloxamer 188 and 0.002% polysorbate 80. Such combinations are described in co-owned, co-pending PCT application Ser. No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Other aspects and advantages of the present invention will be understood upon consideration of the following illustrative examples. Example 1 addresses the effect of BPI protein product administration on mortality associated with meningococcemia. Example 2 addresses the effect of BPI protein product administration on morbidities associated with meningococcemia. Examples 3 and 4 describe the effect of BPI protein product administration on the course of meningococcemia in two particular individuals.

EXAMPLE 1

Clinical Study Protocol—Effect of BPI Protein Product on Mortality

A human clinical study was designed to examine the effect of an exemplary BPI protein product, $rBPI_{21}$, on clinical outcome in pediatric patients suffering from severe systemic meningococcal disease. Clinical outcomes (mortality, amputations, grafts, permanent neurologic impairment) were assessed through study day 28 or discharge, whichever occurred first. Additionally, the safety, pharmacokinetics and hemodynamic effects of the BPI protein product were assessed.

Thus, a Phase I open-label multicenter study of the effects of BPI protein product on pediatric patients with severe meningococcemia receiving standard care was implemented. Patients who met eligibility criteria were enrolled following informed consent of the parent or legal guardian. The eligibility criteria were such that the patients enrolled had a 90% predicted rate of severe adverse outcome, defined as death, stroke, amputation, or skin grafting. All patients received comprehensive pediatric intensive care consistent with the usual standard of care, and received their first dose of antibiotics no more than 8 hours prior to the beginning of BPI protein product administration.

The first four patients received an infusion of 0.5 mg/kg $rBPI_{21}$ over 30 minutes, followed immediately by a continuous infusion of $rBPI_{21}$, at a rate of 0.5 mg/kg/day for 24 hours. The next six patients received an infusion of 1.0 mg/kg $rBPI_{21}$, over 30 minutes, followed immediately by a continuous infusion of $rBPI_{21}$ at a rate of 1.0 mg/kg/day for 24 hours. The remaining patients received an infusion of 2.0 mg/kg $rBPI_{21}$ over 30 minutes, followed immediately by a continuous infusion of $rBPI_{21}$ at a rate of 2.0 mg/kg/day for 24 hours. All study centers escalated to the higher dose levels at the same time.

The pharmacokinetics of the BPI protein product and circulating endotoxin levels were assessed by serial monitoring of plasma for $rBPI_{21}$, and endotoxin by limulus amoebocyte lysate (LAL) assay. Any acute hemodynamic effects associated with administration of $rBPI_{21}$, were described by recording standard hemodynamic parameters, including: heart rate, invasive systemic arterial blood pressure, electrocardiogram, oxygen saturation, and invasive hemodynamic measurements obtained from a pulmonary artery catheter. No new invasive devices were placed for the purposes of the study; the placement of medical devices was at the sole discretion of the attending physician and his/her staff, and only for the purpose of monitoring the patient consistent with normal standards of care.

Safety was monitored by continuous measurements of vital signs and hemodynamics, physical examinations and pre- and post-treatment safety laboratory assessments. Patients were followed for safety until death, hospital discharge or study day 28, whichever occurred first.

Patients with severe meningococcemia were selected for enrollment in the study if they met the following inclusion and exclusion criteria. Inclusion criteria were: (1) age 1 year to 18 years inclusive; (2) presumptive diagnosis of meningococcemia, based on any or all of the following: (a) petechiae or purpura, fever, and hemodynamic instability in a clinical context consistent with the diagnosis of meningococcemia, (b) demonstration of gram-negative diplococci in blood, cerebrospinal fluid, or skin lesions in a clinical context consistent with the diagnosis of meningococcemia, and/or (c) demonstration of meningococcal antigens by immunologic determination in a clinical context consistent with the diagnosis of meningococcemia; (3) Glasgow Meningococcal Septicemia Prognostic Score of 8 or greater [Sinclair et al., supra]; (4) patient history of having received the first dose of antibiotics no more than 8 hours prior to beginning BPI protein product administration; (5) negative pregnancy test for pubertal or post-pubertal females; (6) written informed consent obtained from the parent or legal guardian; and (7) collection of confidential patient follow-up information. Exclusion criteria were: (1) insufficient vascular access to administer BPI protein product without compromising routine ICU care; (2) exposure to investigational agents during the last 30 days prior to study entry; and (3) any condition that in the attending physician's judgment would make the patient unsuitable for participation in the study, including imminent mortality.

The following were performed within 24 hours prior to enrollment in the study: (1) medical history, (2) complete physical examination, (3) chest x-ray, (4) laboratory evaluation: Hematology: CBC, differential; Coagulation: PT, PTT, fibrinogen, D-Dimers; Microbiology: cultures, Gram stains, serology as indicated; Chemistries: sodium, potassium, chloride, bicarbonate, glucose, BUN, creatinine, ionized calcium, phosphorus, magnesium, bilirubin, AST, ALT, CPK (with isoenzymes), LDH; Arterial Blood Gases; Urinalysis: chemistry and microscopic; and (5) procurement of written informed consent and collection of confidential follow-up information.

The $rBPI_{21}$, was supplied as a clear, colorless, sterile non-pyrogenic solution in 10 mL single use glass vials at a concentration of 2 mg/mL in 5 mM sodium citrate/0.15 M sodium chloride buffer, pH 5.0 with 0.2% poloxamer 188 and 0.002% polysorbate 80 containing no preservative. For storage, the $rBPI_{21}$ vial was refrigerated at 2–8° C. at all times prior to administration. The product was brought to room temperature prior to infusion, and was administered via a central vein or other suitable vein. Suitability of intravenous access was determined by easy withdrawal of blood from the access, as well as easy infusion of intravenous fluids without infiltration. $rBPI_{21}$, was the sole agent administered in the chosen port during the course of the infusion protocol. The venous access port was not heparinized, but was flushed as necessary with physiologic saline.

After BPI protein product infusion had started, patients were bserved for the possible development of adverse events. Plasma samples for determination of $rBPI_{21}$ levels were collected immediately prior to the start of the infusion (time zero) and at the following times after the start of the infusion: 30 min., 90 min., 240 min., 720 min., just prior to termination of infusion at 24 hours 30 min., 24 hours 37 min., 24 hours 45 min., 25 hours, 25 hours 30 min., 26 hours 30 min., 27 hours 30 min., and 48 hours. Plasma samples for determination of endotoxin levels were drawn immediately prior to the onset of the infusion (time zero) and at the following times after the start of the infusion: 30 min., 90 min., 240 min., 720 min. and at 48 hours. Serum ionized calcium concentrations were determined immediately prior to the onset of the infusion (time zero) and at the following times after the start of infusion: 30 min., 2 hours, 6 hours, 12 hours, and 24 hours. Monitoring the ionized calcium concentrations is the usual standard of care in meningococcemia and normally occurs every 4 hours. All samples were obtained via a line not used to infuse BPI protein product.

The following vital signs were recorded every 5 min. for thirty min. prior to beginning the infusion, every 5 min. during the 30-min. loading dose, and every 30 min. thereafter for 24 hours: (a) heart rate; (b) systemic arterial blood pressures: systolic, diastolic, and mean; and (c) respiratory rate (if the patient was spontaneously breathing). In addition to the manual collection as outlined above, data was digitally recorded and stored every minute within the bedside monitor during the ICU stay. Once the patient left the ICU, vital signs were collected daily until hospital discharge.

The following invasive hemodynamic parameters were recorded every 10 min. for the 30 min. prior to beginning the infusion, every 10 min. during the 30-min. loading dose, and every 2 hours thereafter for 24 hours: (a) mixed venous oxygen saturation (oximetric catheters only); (b) pulmonary artery wedge pressure; (c) pulmonary artery pressures: systolic, diastolic, mean; (d) cardiac index (CI); (e) systemic vascular resistance index (SVRI); (f) pulmonary vascular resistance index (PVRI); and (g) stroke volume index (SVI). A complete profile of medications and vasoactive infusions was recorded through hospital discharge. The following were documented with a frequency determined by the primary care physician consistent with standard management of severe meningococcal disease: (a) arterial blood gases, (b) venous blood gases, (c) oxygen delivery ($DO_2$) (d) oxygen consumption ($VO_2$), (e) hematology, (f) coagulation, and (g) blood chemistries. The PRISM Score (Pediatric Risk of Mortality Score) was also calculated and recorded at the end of the first hospital day. Table 1 below shows the factors with the corresponding number of points used to calculate the PRISM score (Pollack et al., "The pediatric risk of mortality (PRISM) score," *Critical Care Medicine* 16:1110, 1988).

TABLE 1

Pediatric Risk of Mortality Score (PRISM Score)

AGE RESTRICTION AND RANGES

| FACTORS | Infants only | Children only | All Ages | Pts |
|---|---|---|---|---|
| Systolic BP (mm/Hg) | 130–160 | 150–200 | | 2 |
| | 55–65 | 65–75 | | 2 |
| | >160 | >200 | | 6 |
| | 40–54 | 50–64 | | 6 |
| | <40 | <50 | | 7 |
| Diastolic BP (mm Hg) | | | >110 | 6 |
| Heart Rate (beats/min) | >160 | >150 | | 4 |
| | <90 | <70 | | 4 |
| Respiratory Rate (breaths/min) | 61–90 | 51–70 | | 1 |
| | >90 | >70 | | 5 |
| | APNEA | APNEA | | 5 |
| $PaO_2/FiO_2$ | | | 200–300 | 2 |
| | | | <200 | 3 |
| $PaCO_2$ (mm Hg) | | | 51–65 | 1 |
| | | | >65 | 5 |

TABLE 1-continued

Pediatric Risk of Mortality Score
(PRISM Score)

AGE RESTRICTION AND RANGES

| FACTORS | Infants only | Children only | All Ages | Pts |
|---|---|---|---|---|
| Glasgow score | | | <8 | 6 |
| Pupillary Reactions | | | Unequal or dilated | 4 |
| | | | Fixed and dilated | 10 |
| PT/PTT | | | >1.5 × Control | 2 |
| Total Bilirubin (mg/dl) | | | >3.5 at age >1 month | 6 |
| Potassium (meq/l) | | | 3.0–3.5 | 1 |
| | | | 6.5–7.5 | 1 |
| | | | <3.0 | 5 |
| | | | >7.5 | 5 |
| Calcium (mg/dl) | | | 7.0–8.0 | 2 |
| | | | 12.0–15.0 | 2 |
| | | | <7.0 | 6 |
| | | | >15.0 | 6 |
| Glucose (mg/dl) | | | 40–60 | 4 |
| | | | 250–400 | 4 |
| | | | <40 | 8 |
| | | | >400 | 8 |
| Bicarbonate (meq/l) | | | <16 | 3 |
| | | | >32 | 3 |

At the end of the study (i.e., study day 28 or at time of discharge, whichever occurred first), a physical exam, including vital signs, and a review of any adverse events were performed. The following clinical outcomes were also assessed: (a) mortality; (b) amputations; (c) ging procedures; (d) permanent neurologic impairment including but not limited to cerebrovascular accidents, cerebral atrophy, and seizures requiring medication that manifested as impaired neurologic function; and (e) pediatric outcome scores (based on the Pediatric Cerebral Performance Category Scale and/ or the Pediatric Overall Performance Category Scale, as described by Fiser, "Assessing the outcome of pediatric intensive care," *J. Pediatrics* 121:1 68–74, 1992).

A review was conducted of the medical records of patients admitted to one participating clinical center, Study Center 1, during the two years immediately prior to the initiation of the BPI study. From these records, 14 children were selected for comparative analysis because they met the first three above-described inclusion criteria regarding age, presumptive meningococcemia diagnosis and Glasgow score. Six of these 14 "historical control" children died. This high mortality rate was expected, considering that the inclusion criteria required a Glasgow score of 8 or greater. A Glasgow score of 8 or greater always indicates severe disease.

In striking contrast, none of the 10 patients in the BPI study at Study Center 1 died. Thus, the administration of BPI protein product dramatically reduced the mortality rate of severe pediatric meningococcemia at Study Center 1 from 43% to 0%. When results from all of the participating clinical centers are included, of the 14 total patients enrolled in the BPI study so far, only one patient has died—a mortality rate of only 7%. This low mortality rate is particularly remarkable considering that 12 of the 14 patients had a Glasgow score of 10 or greater when they entered the study. Multiple analyses that calculated expected mortality for the 14 patients in the BPI study, based on indicators (levels of endotoxin, TNF, IL-6 and fibrinogen, and FM) that have been shown to correlate with disease severity and outcome in various studies [Brandtzaeg et al., supra, Van Deuren et al., supra, McManus et al., supra, and Bone, supra] predicted a mortality rate ranging from about 20% to about 50% for this population. Endotoxin, TNF and IL-6 levels for the initial 10 patients in the BPI study are shown in FIGS. 1–6.

EXAMPLE 2

Effect of BPI Protein Product on Morbidity

The clinical outcomes of patients treated in accordance with the BPI protein product study protocol described in Example 1 above are summarized in Table 2 below and compared with the clinical outcomes of the 14 "historical control" children at Study Center 1 who would have met the study's inclusion criteria during the two years immediately prior to the initiation of the study. The natural history of the clinical course of meningococcemia would have been largely similar; previously healthy children underwent a 12–24 hour flu-like prodrome, developed purpura, and then died or became moribund within 4–6 hours. Typically, such meningococcemia patients continue to become sicker in the PICU, at least for the first 12 hours, and often succumb to irreversibly progressive shock. There were no known differences in the standard of care provided to the patients enrolled in the BPI study compared to the 14 previous "historical control" patients at Study Center 1, with the exception of BPI protein product administration.

TABLE 2

| | "Historical Control" Children at Study Center 1 | BPI Study Children at Study Center 1 | BPI Study Children at All Centers |
|---|---|---|---|
| No. Satisfying Inclusion Criteria or Enrolled in BPI Study | 14 | 10 | 14 |
| No. of Deaths | 6 (43%) | 0 (0%) | 1 (7%) |
| Morbidities | | | |
| No. of Survivors With Severe Amputations | 2/8 (25%) | 1/10 (10%) | 1/13 (8%) |
| No. of Survivors With Permanent Neurologic Impairment | 2/8 (25%) | 0/10 (0%) | 0/13 (0%) |
| Total Morbidity Events (severe amputation or permanent neurologic impairment) | 4/8* (50%) | 1/10 (10%) | 1/13 (8%) |

*One patient experienced both severe amputations and permanent neurologic impairment.

The results summarized in Table 2 show that administration of BPI protein product not only vastly reduced the mortality rate at Study Center 1, but also reduced the incidence of severe morbidities from 50% to 10% at Study Center 1. When results from all of the participating clinical centers are included, the overall severe morbidity rate remains low, at 8%. Interpretation of morbidity data from this study is somewhat complicated by the fact that BPI protein product treatment had a significant effect on reducing the number of mortalities associated with this disease, that is, a number of the severely ill patients were rescued who would have otherwise succumbed to the disease. No analysis was performed to predict the morbidities patients would have experienced had they not died. For this morbidity outcome analysis, amputations at the wrist or above, or at the ankle or above, were considered to be severe amputations. Neurologic abnormalities that resulted in significant and permanent impairment of motor, cognitive or sensory function were considered to be permanent neurologic impairments. Four additional BPI study patients (all at Study Center 1) experienced minor amputations of toes or fingers (and one partial foot amputation). Four additional "historical control" patients at Study Center 1 experienced other neurologic abnormalities, including cerebrovascular accidents, seizures, CT scan or EEG abnormalities, and cranial nerve palsy. One BPI study patient (at Study Center 1) experienced a neurologic abnormality (see Example 4).

EXAMPLE 3

Clinical Course of One Individual in the BPI Study

This patient (number 2 in the BPI study) was a seven year old white male who was previously healthy. On the night prior to admission to the pediatric intensive care unit (PICU), he came to the emergency room with symptoms of fever, vomiting, and headache. His white blood cell count (WBC) was 17,500, but he was sent home because his exam was not suggestive of significant disease. He was seen again the next morning, when a diffuse petechial rash was noted. His WBC had dropped to 6,300, and his fever and headache had worsened. Meningococcemia was suspected, and after initial fluid infusion and antibiotic administration, he was admitted to the Pediatric Intensive Care Unit (PICU) at Study Center 1.

He was intubated and mechanically ventilated, fluid resuscitated, and begun on inotropic support with an epinephrine infusion. He was treated with the antibiotic ceftiaxone. Before enrollment in the BPI study, his Glasgow score was 14/15, his PRISM score was 17, and his physical exam revealed a temperature of 38.8° C., a heart rate of 145, a respiratory rate of 16 on the ventilator, and a blood pressure of 107/46. His PTT value was 25.2 and his fibrinogen level was 480. Blood cultures revealed $N.$ $meningitdis$ serotype C. A pulmonary artery catheter was placed for monitoring, and written informed consent was obtained for the BPI protocol described above in Example 1.

An $rBPI_{21}$ infusion was started at 14:35 on the day of admission to PICU (Day One). He received a dose of 0.5 mg/kg $rBPI_{21}$ over 30 minutes followed by an infusion of 0.5 mg/kg over the following 24 hours. He tolerated his infusion well with no hemodynamic changes or other complications. His PICU course was relatively uneventful; his inotropic support was discontinued on the night of Day Four, after which his ventilator was rapidly weaned. He was taken off the ventilator during Day Five without any problems. He was transferred to the general pediatric wards on the afternoon of Day Six and discharged from the hospital on Day Nine without any complications.

EXAMPLE 4

Clinical Course of Another Individual in the BPI Study

This patient (number 6 in the BPI study) was an 18 year-old white male who was previously in excellent health. Prior to admission, he experienced a two-day history of sore throat and lethargy. On the evening of admission, his roommate found him in the corner of his dormitory room, unresponsive and covered with a purple petechial rash. He was transported via ambulance to the hospital, at which time his temperature was 101° F. and he was in fulminant shock. He was treated with fluid resuscitation, ceftriaxone antibiotic, and a dopamine infusion to improve circulation. He was transported via helicopter to Study Center 1.

On arrival, he was intubated and ventilated. Before enrollment in the BPI study, his Glasgow score was 12/15 and his PRISM score was 16.He was moribund. His physical exam was significant for rapidly expanding diff-use purpura, a capillary refill greater than eight seconds, and minimally detectable pulses. His feet were blue, cold, and pulseless, as were all ten fingers. He had a temperature of 37.7° C., a heart rate of 150, a respiratory rate of 20 on the ventilator, and a blood pressure of 133/66. His laboratory evaluation was significant for a WBC of 7,500 with a differential of 73% segs and 14% bands. His PT was 26, his PTT was greater than 114, his fibrinogen level was 121, and his D-dimers were greater than 8.Cerebrospinal fluid cultures revealed $N.$ $meningitidis$ serotype C. He had biochemical evidence of multi-organ system failure on arrival. Fluid resuscitation continued and an epinephrine infusion was begun. Informed consent was obtained and he was enrolled in the BPI study according to Example 1 above.

An $rBPI_{21}$, infusion at a dose of 1 mg/kg over 30 minutes was begun at 07:15 on the day of his admission to PICU (Day One), followed by a dose of 1 mg/kg over the next 24 hours. The $rBPI_{21}$, infusions were well tolerated without adverse hemnodynamic effects. He required hemodynamic support with inotropic infusions of dopamine, dobutamine and epinephrine. He was weaned off of epinephrine and dopamine on the morning of Day Three, and rapid weaning of his dobutamine followed. Invasive evaluation of his hemodynamic status with a Swan-Ganz catheter revealed a hyperdynamic state which did not undergo transition to hypodynamic state, as would be typical of such severely ill children on day two of therapy. Although his coagulopathy was initially severe and required multiple transfusions of fresh frozen plasma, packed cells, and platelets, the coagulopathy had rapidly resolved by Day Three of hospitalization. Also by Day Three, his initial cold and unperfused feet began to return to a normal pink color, with evidence of warmth and circulation being restored. Additional antibiotic therapy with vancomycin and tobramycin was begun. On Day Four his clinical status had improved to the point that his ventilator was weaned. The ventilatory wean continued throughout that day, but this wean was interrupted on Day Five by transient pulmonary edema. This pulmonary edema was believed due to resorption of third spaced fluid and healing of his vascular leak. His ventilator wean was continued later on Day Five. His circulation in his lower extremities had markedly improved to the point that upon his discharge from PICU on Day Eight, tissue injury was only evident in his left heel, which was debrided, and his left second toe, which was ultimately amputated. During his hospital course, following an episode of transient hypertension, he underwent a CT-scan which revealed evidence of a right temporal/parietal cerebrovascular accident (CVA) which dated approximately to the date of his admission to PICU. The CVA was neurologically silent and did not compromise any motor, cognitive, or sensory functions. His post-PICU stay on the pediatric ward consisted primarily of physical therapy, occupational therapy, and enhanced nutrition. He was discharged on Day Fourteen to a rehabilitation facility for further work on strengthening and general rehabilitation.

Numerous modifications and variations of the above-described invention are expected to occur to those of skill in the art. Accordingly, only such limitations as appear in the appended claims should be placed thereon.

What is claimed is:

1. A method of reducing mortality associated with meningococcemia comprising the step of administering a therapeutically effective amount of a bactericidal/permeability-increasing (BPI) protein product to a human suffering from meningococcemia.

2. The method of claim 1 wherein the BPI protein product is an amino-terminal fragment of BPI protein having a molecular weight of about 21 kD to 25 kD.

3. The method of claim 1 wherein the BPI protein product is rBPI$_{23}$ or a dimeric form thereof.

4. The method of claim 1 wherein the BPI protein product is rBPI$_{21}$.

5. A method of treating a human suffering from meningococcemia comprising the step of administering BPI protein product in an amount effective to reduce the number or severity of morbidities.

6. The method of claim 5 wherein the morbidities are selected from the group consisting of severe amputations, grafting procedures and permanent neurologic impairment.

7. The method of claim 5 wherein the BPI protein product is an amino-terminal fragment of BPI protein having a molecular weight of about 21 kD to 25 kD.

8. The method of claim 5 wherein the BPI protein product is rBPI$_{23}$ or a dimeric form thereof.

9. The method of claim 5 wherein the BPI protein product is rBPI$_{21}$.

* * * * *